United States Patent [19]

Coulaloglou et al.

[11] 4,247,987
[45] Feb. 3, 1981

[54] CONTINUOUS COUNTERCURRENT FLUID-SOLIDS CONTACTING PROCESS STABILIZED BY A MAGNETIC FIELD

[75] Inventors: Costas A. Coulaloglou, Morristown; Jeffrey H. Siegell, Westfield, both of N.J.

[73] Assignee: Exxon Research & Engineering Co., Florham Park, N.J.

[21] Appl. No.: 79,219

[22] Filed: Sep. 26, 1979

[51] Int. Cl.³ .............................................. F26B 3/08
[52] U.S. Cl. ............................................. 34/1; 34/10; 34/57 A; 34/102; 423/DIG. 16; 432/15
[58] Field of Search .................. 252/411 R; 34/1, 10, 34/57 A, 102; 423/DIG. 16; 406/89, 90; 432/15, 58

[56] References Cited

U.S. PATENT DOCUMENTS

| 2,641,063 | 6/1953 | Greiman | 34/102 |
| 3,028,681 | 4/1962 | Jorman et al. | 34/57 A |
| 3,700,421 | 10/1972 | Johnson et al. | 422/139 |
| 4,115,927 | 9/1978 | Rosensweig | 422/139 |
| 4,136,016 | 1/1979 | Rosensweig | 34/1 |

Primary Examiner—Larry I. Schwartz
Attorney, Agent, or Firm—Albert P. Halluin

[57] ABSTRACT

The present invention relates to a process for continuous countercurrent contacting with magnetically stabilized fluidized beds. More particularly, the invention relates to the operation of a magnetically stabilized bed with continuous solid addition and removal. The bed particles which include a magnetizable component are stabilized against gas by-passing and solids back-mixing (except possibly for the flow or movement of the solids near entrance or exit ports or near fluid injection zones) during countercurrent contacting by the use of an applied magnetic field. The process of the invention is particularly suited for carrying out separation processes. The use of the applied magnetic field in such processes enables one to use small size fluidizable, adsorbent particles without encountering high pressure drops. The small adsorbent particles having a magnetic component give faster transfer of the sorbed species from the contacting fluid than with larger adsorbent particles which allows for a closer approach to equilibrium.

25 Claims, 6 Drawing Figures

CONTINUOUS COUNTERCURRENT FLUID-SOLIDS CONTACTING PROCESS STABILIZED BY A MAGNETIC FIELD

FIELD OF THE INVENTION

The present invention relates to a process for continuous countercurrent contacting with magnetically stabilized fluidized beds. More particularly, the invention relates to the operation of a magnetically stabilized bed with continuous solids addition and removal. The bed particles which include a magnetizable component are stabilized against gas by-passing and solids back-mixing (except possibly for the flow or movement of the solids near entrance or exit ports or near fluid injection zones) during countercurrent contacting by the use of an applied magnetic field. The process of the invention is particularly suited for carrying out separation processes. The use of the applied magnetic field in such processes enables one to use small size fluidizable, adsorbent particles without encountering high pressure drops. The small adsorbent particles having a magnetic component give faster transfer of the sorbed species from the contacting fluid than with larger adsorbent particles which allows for a closer approach to equilibrium.

DESCRIPTION OF THE PRIOR ART

Numbers of workers have studied the influence of magnetization on the dynamics of fluidized solids in batch beds. An early account of this phenomena was reported by M. V. Filippov [Applied Magnetohydrodynamics, *Trudy Instituta Fizika Akad. Nauk.*, Latviiskoi SSR 12: 215–236 (1960); *Zhurnal Tekhnicheskoi Fiziki*, 30, (9): 1081–1084 (1960); *Izvestiya Akad. Nauk.*, Latviiskoi SSR, 12 (173): 47–51 (1961); *Izvestiya Akad. Nauk.*, Latviiskoi SSR, 12: 52–54 (1961); and Aspects of Magnetohydrodynamics and Plasma Dynamics, Riga (1962), *Izvestiya Akad. Nauk.*, Latviiskoi SSR, pp. 637–645]. Subsequent workers have reported on the influence that magnetization exerts on pulsations, heat transfer, structure, and other characteristics of magnetized and fluidized solids in batch beds. A review of some of this work is given by Bologa and Syutkin [*Electron Obrab Mater*, 1: 37–42 (1977)]. Ivanov and coworkers have described some benefits of using an applied magnetic field on fluidized ferromagnetic solids in the ammonia synthesis process and some of the characteristics of the bed for this process [see British Pat. No. 1,148,513 and numerous publications by the same authors, e.g., Ivanov et al, *Kinet. Kavel*, 11 (5): 1214–1219 (1970); Ivanov et al, *Zhurnal Prikladnoi Khimii*, 43, 2200–2204 (1970); Ivanov et al, *Zhurnal Prikladnoi Khimii*, 45: 248–252 (1972); Ivanov et al, *Chemical Industry*, 11: 856–858 (1974); Shumkov et al, *Zhurnal Prikladnoi Khimii*, 49 (11): 2406–2409 (1976)]. Various means for operating magnetic fields to stabilize a bed of magnetizable solids have been disclosed in U.S. Pat. Nos. 3,440,731, 3,439,899, 4,132,005 and 4,143,469, and Belgium Pat. No. 865,860 (published Oct. 11, 1978).

Recently, R. E. Rosensweig [*Science*, 204: 57–60 (1979), *Ind. Eng. Chem. Fundam.*, 18 (3): 260–269 (1979) and U.S. Pat. Nos. 4,115,927 and 4,136,016] reported on a number of features of magnetically stabilized fluidized magnetizable solids and a systematic interpretation of the phenomena. In these publications and patents, R. E. Rosensweig reported on the quiescent yet fluid-like state of the magnetically stabilized (fluidized) bed (MSB), particularly one which is totally free of bubbles or pulsations when a uniform magnetic field is applied to a bed of magnetizable solids colinear with the direction of the fluidizing gas flow. As such, this magnetic stabilization produces a non-bubbling fluid state having a wide range of operating velocities denoted as a superficial fluid velocity ranging between (a) a lower limit given by the normal minimum fluidization-superficial fluid velocity required to fluidize the bed of solids in the absence of the applied magnetic field, and, (b) an upper limit given by the superficial fluid velocity required to cause time-varying fluctuations of pressure difference through the stabilized fluidized bed portion during continuous fluidization in the presence of the applied magnetic field. It is disclosed in Rosensweig's U.S. Pat. No. 4,115,927 that the stably fluidized solids resemble a liquid and as such enjoy the benefits that the solids are facilitated for transport while concomitantly the pressure drop is limited to that of a fluidized bed. In addition, the beds exhibit the absence of backmixing as normally associated with fixed bed processes. In col. 6, lines 63–66 of the '927 patent, it is stated: "The fluidized bed thus formed has many properties of a liquid; objects float on the surface and the addition or withdrawal of solid particles in process equipment is also facilitated." The '927 patent further states that "(o)rifice discharge tests confirm the ability to transfer solids out of the containing vessel" (column 8, lines 58–59). Further, in column 21, lines 17–24, it is stated: "The utility of the magnetically stabilized compositions in applications such as ab- or adsorptive separation of vapor species, catalyst utilization and regeneration, particulate filtration and subsequent bed cleaning, reaction of solids in moving beds and allied applications in which bed solids must be transported to and from the bed depend on the fluidized solids behaving as a medium capable of flowing in response to a pressure differential."

While Rosensweig disclosed the possibility of transporting the solids in a magnetically stabilized bed from vessel to vessel, all of the reported experiments involved batch beds. In addition, neither Rosensweig nor Filippov reported on the effect on the locus of transition between the bubbling fluidized and stabilized regions in beds which have continuous solids addition and removal. Therefore, the boundaries of the established regions as defined by Rosensweig and Filippov have not been taught for a process where solids are continuously added and removed. The present invention is concerned with the operation of a magnetically stabilized bed with continuous solids addition and removal at or substantially near the locus of transition between the bubbling and stabilized region in the bed. It has been discovered that when the magnetically stabilized bed is operated at or substantially near the locus of transition between the bubbling and stabilized region in the bed, the bed solids have greater fluidity. This greater fluidity facilitates the movement of solids within the vessels and transfer from vessel to vessel.

SUMMARY OF THE INVENTION

The present invention is directed to an improved process for effecting fluid-solids contacting under fluidization conditions wherein a bed of suspended magnetizable particles are contacted in a contacting chamber with an opposing fluid stream which passes through said bed in an ascending manner, said bed being structured or stabilized by an applied magnetic field having a strength sufficient to suppress solids backmixing, the improvement which comprises: passing said bed of suspended magnetizable particles in a descending manner substantially countercurrent to said contacting stream and removing said magnetizable particles from said contacting vessel, said process being operated in a manner such that the ratio of the difference between the transition velocity and the operating velocity to the difference between the transition velocity and the normal minimum fluidization velocity ranges between −0.1 and +0.5. In some processes, the bed particles may be recirculated back into said contacting chamber for further countercurrent contacting with said fluid stream. The magnetizable particles may be continuously removed from said contacting vessel to a second contacting vessel, although this removal may be intermittent, and thereafter recirculating the magnetizable particles from the second contacting vessel to the first contacting vessel for further contacting. The particles to be contacted may be passed through the contactor in a single pass mode, i.e., an iron ore reduction processor, or a solids drying process.

The magnetizable solids preferably move through the contacting vessels in a plug-flow manner countercurrently against the ascending flow of the fluidizing medium. The fluidizing medium flows at a sufficient superficial velocity to suspend or levitate the magnetizable particles against the force of gravity under the influence of fluid dynamic drag, but below the superficial velocity which will cause solids backmixing. The bed may be operated in the bubbling mode which will be desired for some processes where heat transfer is desired. However, it is generally preferred to apply the magnetic field at a sufficient strength to suppress substantial bubble formation in the bed. In any event, the strength of the applied magnetic field is such as to prevent solids backmixing, but at a weak enough magnetic field strength at a given fluid velocity to achieve a maximum fluidity ratio. The fluidity ratio defined as:

$$U_T - U_{OP}/U_T - U_{mf}$$

should range between −0.1 and +0.5, preferably between −0.05 and +0.2, more preferably between −0.01 and +0.1, where $U_T$ is the superficial fluid velocity required to cause time-varying fluctuations of pressure difference through the bed in the presence of the applied magnetic field, $U_{mf}$ is the normal minimum fluidization superficial fluid velocity required to fluidize the bed of magnetizable particles in the absence of an applied magnetic field, and $U_{OP}$ is the actual operating superficial fluid velocity.

The process of the present invention is applicable to a variety of processes such as particulate removal of solids, catalytic conversions, sorption processes, gas separation processes, etc.

BRIEF DESCRIPTION OF THE DRAWINGS

FIG. 3 includes an additional magnetically stabilized region below the main contacting vessel which can be used as a pre-desorber or pre-regenerator section.

DESCRIPTION OF THE PREFERRED EMBODIMENTS

Figure 1:
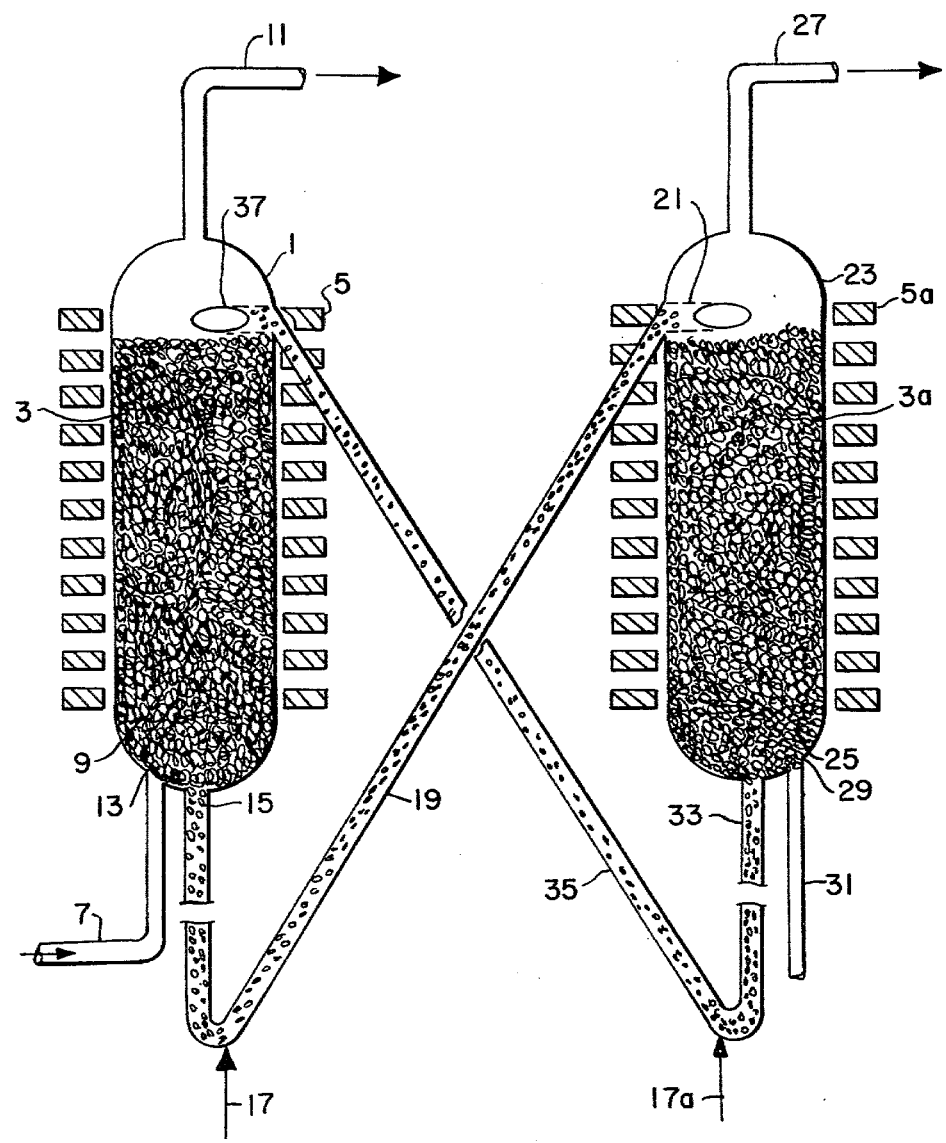
FIG. 1 represents a vertical cross-sectional view of two magnetically stabilized contacting vessels which are positioned side by side.

The process of the invention is preferably carried out by fluidizing the magnetizable particles under countercurrent plug flow conditions by subjecting the particles to a magnetic field, preferably a uniform applied magnetic field having a substantial component along the direction of the external force field (e.g., gravity) such that the magnetizable particles have a component of magnetization along the direction of the external force field and wherein at least a portion of the bed of particles is levitated (fully supported) by a flow of fluid opposing said external force field at a superficial fluid velocity and particle magnetization such that the fluidity ratio defined as:

$$U_T - U_{OP}/U_T - U_{mf}$$

ranges between −0.1 and +0.5, preferably between −0.05 and +0.2 and more preferably between −0.01 and +0.1, wherein $U_T$, $U_{mf}$ and $U_{OP}$ are as previously defined. The magnetization of the magnetizable particles will not be sufficient to cause substantial particle-to-particle agglomeration as this will decrease the overall fluidity of the bed particles. Preferably the strength of the magnetic field and its deviation from a vertical orientation are maintained so as to prevent and/or suppress the formation of bubbles in the fluidized media at a given fluid flow rate and with a selected fluidized particles makeup. The magnetically stabilized fluidized beds have the appearance of expanded fixed beds with no gross solids recirculation (except for the plug flow movement through the vessels) and very little or no gas bypassing. The application of the magnetic field enables one to employ superficial fluid flow rates 2, 5, 10 or 20 times or more the flow rate of the fluidized bed at incipient fluidization in the absence of the applied magnetic field, concomitant with the substantial absence of gross solids circulation. In other words, as the superficial fluid velocity is increased, the pressure drop through the bed is similar to that which would be expected from a normal fluidized bed without the application of a magnetic field, it increases to the bed weight support value at the minimum fluidization velocity, and then remains relatively constant as the fluid velocity is increased. This stably fluidized bed condition persists even as the solids are continuously added and removed in a descending, plug flow manner through the contacting vessel.

An important feature of invention resides in the discovery that the fluidity of the bed of magnetized particles in the stable region continuously decreases from the fluidity at the bubbling or transition fluidization velocity as the magnetic field is increased above, or the superficial fluid velocity is decreased below the value at transition. Thus, in the case of moving beds, it is desirable to operate close to the locus of points of transition between the stable non-bubbling bed and the bubbling region in order to take advantage of the increased fluidity.

The fluidity of the bed can be determined by measuring the angle of repose of the bed particles at given superficial gas velocities and particle magnetization. Such experimental measurements have shown that by increasing the particle magnetization or decreasing the superficial gas velocity from the transition point increases the angle of repose. Thus, to operate the fluidized bed with increased bed fluidity, one should operate at low particle magnetization or high gas velocities (i.e., as close to transition as possible). In any event, the particle magnetization for the particular particles used should be insufficient to cause substantial stiffening of the bed, i.e., the point at which the bed medium develops an appreciable resistance to flow.

The magnetically stabilized bed thus described can combine in one system the principal advantages of both fluid beds and fixed bed reactor systems. Listed in Table I are a number of desirable features and characteristics for a good contactor or reactor system. For example, with small particle size diffusional resistance within a bed particle can be reduced and the catalyst or sorbent used more effectively. Concomitantly, both high pressure drop and gross gas bypassing are eliminated. By practice of the process of the instant invention, all of these features can be achieved in a single system. Also with the magnetically stabilized bed several steps or operations can be combined in the single reacting system; for example, simultaneous reaction and gas to particle heat exchange, particulate removal plus chemical reaction, etc. In addition, since the stabilized beds are mobile and the bed solids are circulated, it is possible to carry out continuous reactions with frequent regenerations so that catalysts or sorbent activity can be restored on a very short cycle.

TABLE I

| MSB Combines Principal Advantages of Fluid Beds and Fixed Beds | | | |
|---|---|---|---|
| | Fluid Bed | MSB | Fixed Bed |
| Small particle size with low $\Delta p$ | yes | yes | no |
| Absence of gas bypassing | no | yes | yes |
| Continuous solids throughput | yes | yes | no |
| Countercurrent contacting | no | yes | no |
| Avoids entrainment from bed | no | yes | yes |

The magnetizable solids of the magnetically stabilized bed are preferably flowed downward countercurrent to the fluidizing fluid (preferably a gas or feed vapors) with the piston flow of the stabilized solids permitting close control of sorption and chemical reaction. These features are particularly advantageous for separations in countercurrent gas solids systems that normally require a high degree of staging.

The process of the invention is well suited for removing small contaminant particulates from a gas stream, especially at elevated temperatures and pressures which are beyond the capability of commercial electrostatic precipitators and baghouses. Since the bed is fluid, the contents may be removed for cleaning on a continuous basis, and due to the expanded state of the bed, the pressure drop remains nearly constant in operation even upon collecting several weight percent of fines.

A wide range of magnetizable particles may be employed as the capture medium in the process of the invention. Generally speaking, the capture efficiency increases as a function of higher particle magnetization. Bed depth, applied field and capture time are all important variables. Bed loadings of 3-6 wt. % have been achieved while maintaining 99+% overall efficiency with collected particulates in the range 1-16 microns.

The magnetizable particles used in the process of the present invention must have the proper magnetizable (and in some instances sorption or catalytic) properties. Depending upon the application, a variety of magnetizable particles may be utilized. For noncatalytic operations such as filtering and heat transfer, ferromagnetic solids such as 400 series stainless steels, cobalt, iron and nickel as well as natural ferrites can be used. For catalytic or sorption applications the magnetizable particles may be included in suitable catalyst or sorption particle bases, such as silica, alumina or silica-aluminas. A description for the preparation of the magnetizable sorption particles is described below.

For economy, it is desirable that the bed solids achieve sufficient magnetization to structure or stabilize the bed at a relatively small intensity of applied magnetic field in order that the electromagnet field source be economic. When ferromagnetic particles are placed in the magnetic field, the induced magnetization is a function of the magnetic material, the geometry of the ferromagnetic particle, and the geometry of the bed. The effective field $H_e$ within the magnetic substance can be related to the applied field $H_a$, the ferromagnetic particle magnetization $M_f$, and the demagnetization coefficient of the ferromagnetic particles $d_f$ and that of the bed $d_b$ by the relationship $H_e = H_a - d_b M_b + d_s M_b - D_f M_f$ where $M_b = (1 - \xi_o) M_f$. The value of $d_s$ is constant at $\frac{1}{3}$ so $H_e$ is increased by reducing $d_b$ and $d_f$. Geometry establishes the demagnetization coefficient for axially magnetized cylinders as $d = 1 - [L/D]/[1 + (L/D^2)]^{\frac{1}{2}}$. Thus, a low value of $d_b$ is favored by a bed in which length exceeds diameter.

With proper selection of magnetic particles, the requirement for the electromagnet field source in commercial plants will be modest. Magnet power-dissipation creates heat that is removed using natural convection air cooling. This eliminates any need for liquid convection cooling and attendant requirements for coolant treatment and recirculation. The magnetic field source may be computer designed with high confidence to yield an applied magnetic field having a specified intensity and uniformity.

The invention is not limited by the shape or positioning of the magnet employed to produce the magnetic field. The magnet can be of any size, strength or shape and can be placed above or below the bed to achieve special effects. The magnets employed can be placed within or without the vessel and may even be employed as an integral portion of the vessel structure itself. The process is not limited to any particular vessel material and it can be readily adapted for use in contacting vessels currently employed by industry.

The amount of magnetic field to be applied to the fluidized solids in the contacting zones (adsorption and desorption zones) will, of course, depend on the desired magnetization for the magnetizable particles and the amount of stabilization desired. Particles having relatively weak magnetic properties, e.g., some composites and alloys, will require the application of a stronger magnetic field than particulate solids having strong ferromagnetic properties, e.g., iron, to achieve similar stabilization effects. The size and shape of the solids will also obviously have an effect on the strength of the magnetic field to be employed. However, since the strength of the field produced by an electromagnet can be adjusted by adjusting the current strength of the electromagnet, an operator can readily adjust the field strength employed to achieve the desired degree of stabilization for the particular system employed. Specific methods of applying the magnetic field are also described in U.S. Pat. Nos. 3,440,731; 3,439,899; 4,115,927 and 4,143,469; British Pat. No. 1,148,513 and in the published literature, e.g., M. V. Filippov, Applied Magnetohydrodynamics, *Trudy Instituta Fizika Akad. Nauk.*, Latviiskoi SSR 12: 215–236 (1960); Ivanov et al, *Kinet. Kavel*, 11 (5): 1214–1219 (1970); Ivanov et al, *Zhurnal Prikladnoi Khimii*, 45: 248–252 (1972); and R. E. Rosensweig, *Science*, 204: 57–60 (1979), which are incorporated herein by reference. The most preferred applied magnetic field will be a uniform magnetic field such as described in U.S. Pat. No. 4,115,927. Typically, the empty vessel applied magnetic field, as taught in U.S. Pat. No. 4,115,927, will range from about 50 to about 1500 oersteds, preferably from about 100 to about 600 oersteds and more preferably from about 125 to about 400 oersteds.

As mentioned above, the countercurrent process of the invention is useful in several areas of application, such as particulate filtration, catalytic conversions, and sorption separations. Combination processes give the potential for substantial cost savings, compared to conventional processing involving separate steps.

A brief description of the particulate collection and catalytic reforming processes using the process of the invention are described below while a detailed description of the sorption process follows.

PARTICULATE COLLECTION FROM GASES

The characteristics of the magnetically stabilized beds compared to conventional fluidized solids beds or fixed beds can be used to advantage to remove particulates from gases. The gas bubbles and bypassing which make a conventional fluid bed ineffective for filtration are absent. Compared to a settled bed of small-size solids, the expanded structure of a magnetically stabilized bed can collect a much greater quantity of particulates without tending to plug at the inlet face. The flow properties of the solids facilitate use of a continuous solids-flow system in which the particulate-laden solids flow to another vessel for regeneration.

One specific particulate removal application which would be applicable to the process of the invention involves final cleanup of 925° C. 950 kPa gases from pressurized fluid bed coal combustion, prior to sending the gases to expansion turbines for power recovery in a combined cycle system. In such a process coal, limestone and compressed air are fed to a pressurized fluid bed boiler. The hot gases from the pressurized fluid bed boiler are transported to primary and secondary cyclones to remove ash. The hot gases are then continuously fed into the magnetically stabilized contactor of the invention countercurrently to the flow of solids, aluminized cobalt solids, and 99+% of the incoming particulates are removed.

The particulate-laden solids flow to a bubbling-bed elutriator in which no magnetic field is applied. A small amount of air or steam is used to fluidize this bed and carry the flyash overhead; after partial cooling of the elutriator gas, the particulates can be removed by a conventional electrostatic precipitator. The cleaned hot gases are fed to the turbines for air compression and power generation.

SHORT-CYCLE CATALYTIC REFORMING OF NAPHTHA

Another application which can be practiced by the present invention involves a continuous-solids flow regenerative process for catalytic reforming of naphtha for gasoline octane improvement or aromatics manufacture. General process conditions of temperature, pressure, and recycle gas rate are in the range of other regenerative processes such as cyclic reforming. However, the use of magnetically stabilized beds of much smaller catalyst particles give the following advantages: removes catalyst diffusion limitations; increases activity; makes it feasible to go to much shorter on-oil cycles, e.g., 10 hours, which maintains catalyst activity much faster to freshly regenerated activity and selectivity.

Table II shows the improved activity and selectivity obtained in laboratory with small-size (MSB-size) catalyst in short cycles, compared to conventional catalyst size and cycle length. Activity is 2–3 times as high and $C_5+$ liquid yield is 3% higher on feed.

TABLE II

Small-size MSB Catalytic Reforming Catalyst with Short Cycles Improves Both Catalyst Activity and Selectivity

|  | Conventional Catalyst | MSB Catalyst |
|---|---|---|
| Feed Type | Paraffinic | |
| Octane severity | 100 | . |
| Rec. gas rate, k mol/m$^3$ | 15 | |
| On-oil cycle, h | 100 | 10 |
| Space velocity, w/h/w | 1.1 | 3.2 |
| $C_5+$ yield, LV% | 74.7 | 77.7 |

CONTINUOUS SOLIDS-FLOW MOLECULAR SIEVE SEPARATIONS SYSTEM

In its broadest sense, this aspect of the present invention can be defined as a process for separating a hydrocarbon mixture which comprises countercurrently feeding a hydrocarbon mixture to a bed of adsorbent particles which are admixed or composited with magnetizable particles under fluidization conditions wherein said bed is stabilized by the application of a magnetic field, and recovering the separated hydrocarbon components.

The adsorbent particles may be used as admixtures or as composites with a ferromagnetic or ferrimagnetic substance. All ferromagnetic and ferrimagnetic substances, including, but not limited to, magnetic $Fe_3O_4$, $\gamma$-iron oxide ($Fe_2O_3$), ferrites of the form $MO \cdot Fe_2O_3$, wherein M is a metal or mixture of metals such as Zn, Mn, Cu, etc.; ferromagnetic elements including iron, nickel, cobalt and gadolinium, alloys of ferromagnetic elements, etc., may be used as the magnetizable and fluidizable particulate solids which are used in admixture or composited with the adsorbent particles. Alternatively the adsorbent may itself contain a ferromagnetic or ferrimagnetic substance in its chemical makeup. In this case, the adsorbent is already magnetic; no additional magnetic material need be admixed or composited with the adsorbent.

The adsorbent particles are chosen to suit the particular feed to be treated and the substance that is to be removed from the feed. Inorganic, organic or high molecular weight inorganic or organic adsorbents may be used. It has recently been reported that natural magnetite may be used as an adsorbent in gas-solid chromatography (Journal of Chromatography, 172, 357–361 (1979)).

One class of adsorbents suited for the separation process of the present invention include activated carbons, treated activated carbons, molecular-sieving carbon; selected artificially synthesized zeolites, such as those having some particular ratio of principal components identified as: "Type A"; "Type L"; "Type X"; "Type Y"; "Type ZSM"; mordenite; faujasite; erionite; and the like; those zeolites which have particular silica-alumina ratio and those in which the original sodium cations are exchanged to other cations; selected silica-gels such as those having some particular relative components of silica, alumina and ferric oxides, those which have particular steric properties as the average pore diameter, specific surface area, pore volume and others; selected activated alumina such as those having particular components of aluminum oxide and water, those hydrated forms, some particular crystal forms, those which have a particular structure; activated clay or selected acid clays such as montmorillonite in which case base is exchange holloysite or attapulgite.

These adsorbents comprising carbon, silica, alumina, metal oxides, iron, magnesium, hydrated water and/or other elements are characterized as:

(1) having several different structures, or
(2) having different components, and
(3) such that some composing elements are substituted by others, followed by further chemical or physical treatment.

Most of the aforesaid adsorbents are readily available in the commercial market. Also the adsorbents similar to those which are commercially available can be generally synthesized without very elaborate technique and many adsorbents can be prepared by chemically or physically treating commercially available adsorbents. A further description of the zeolites mentioned above, and their methods of preparation are given, for example, in U.S. Pat. Nos. 2,882,243; 2,882;244; 3,130,007; 3,410,808; 3,733,390; 3,827,968 and patents mentioned therein, all incorporated herein by reference.

Another class of adsorbents include cation-exchange resins with exchange groups of benzene sulfonic acid, carboxylic acid, phosphoric acid; strongly or weakly basic anion-exchange resins; high molecular weight particles of styrene-divinylbenzene copolymer, or its halomethylated, or cyano-ethylated polymers; acrylonitrile copolymers; high molecular weight compounds having several functional groups such as cyano, cyanomethyl, chloromethyl, thioether, sulfone, isocyanate, thiocyanate, thiourea, allyl, acetylacetone, aldehyde, ketone, aliphatic, anhydride, ester, halogen, nitro and others.

The most suitable adsorbents for achieving high adsorption-desorption rates are synthetic zeolites, activated or treated carbon adsorbents and high molecular weight organic materials. These adsorbents generally show high exchange rate of adsorbing components, probably because of their chemical affinity for various contaminant substances such as acid gases and polar molecules, in the case of high molecular weight materials, and because of the macropores in case of synthetic zeolites which comprise minute crystals smaller than a few microns, and clay or other binding material.

Typical examples of suitable adsorbents are synthetic zeolite "Type A" for the separation of various polar molecules from gaseous feeds. Type A zeolite has a typical oxide formula $Na_2O \cdot Al_2O_3 \cdot 2SiO_2 \cdot 4\frac{1}{2}H_2O$, a typical unit-cell formula $Na_{12}[(AlO_2)_{12}(SiO_2)_{12}] \cdot 27H_2O$, a density of 1.99 g/cc, a unit cell constant of 12.32–24.64 Angstroms, a void volume of 0.47 cc/cc, a free aperture of 2.2 Å($\beta$) – 4.2 Å($\alpha$), and a kinetic diameter of 3.6–3.9 Å.

Synthetic zeolites are one of the most useful inorganic adsorbents because the adsorption power of polar molecules onto zeolites can easily be altered by exchanging sodium ions which usually come from the original production steps into some other cations to change their crystal structure or electron configurations to the desired forms. Usually Group I metal ions such as lithium, potassium, rubidium, cesium; silver, copper; Group II metal ions such as beryllium, magnesium, calcium, strontium, barium, zinc, cadmium, mercury, titanium, vanadium, chromium, nickel, cobalt, iron, manganese, rare earth metals, uranium, lead cations or their mixtures are used to replace sodium ions originally contained in the zeolites. The most effective sets of cations are: potassium and lithium; potassium and calcium, potassium and cadmium, potassium and iron; potassium and nickel, potassium and cobalt; potassium and barium; potassium and magnesium; calcium and magnesium; calcium and manganese, lithium and manganese, barium and sodium; barium and lead; iron and uranium; and others. Given a particular feedstream, the most suitable set of cations, their relative compositions, or most effective activation treatments can be easily elected through various experiments, since cation-exchange procedure is readily repeated many times. Generally, Type A synthetic zeolites are exchanged with calcium or magnesium or their mixtures for separating the straight chain hydrocarbons from branched chain hydrocarbons. In processes for the separation of $C_8$ aromatic mixtures and more particularly the separation of paraxylene from admixtures with its isomers and/or ethylbenzene it is preferred to use Type X or Type Y crystalline aluminosilicates such as disclosed in U.S. Pat. Nos. 2,882,244 and 3,130,007. A particularly preferred adsorbent for separation of $C_8$ aromatic mixture is the modified type Y zeolite containing predominantly potassium ions and having a unit cell of 24.50 to 24.75 Angstroms, e.g., such as disclosed in U.S. Pat. No. 3,686,343, the disclosure of which is incorporated herein by reference.

When the magnetizable component is admixed with nonmagnetic adsorbent particles, it is preferred that the volume fraction of the magnetizable component exceed 25 volume percent, more preferably it should exceed 50 volume percent, and preferably more than 60 volume percent, to obtain the greatest bed stability at the lowest applied magnetic field strength.

In case of a composite of the magnetizable component and the adsorbent, the ferromagnetic and/or ferrimagnetic material will comprise 1 to 25, preferably 5 to 15 volume percent based on the total volume of the composite adsorbent. In any event, the composite should have a magnetization of at least 50 gauss, preferably greater than 250 gauss.

The composites of the magnetizable component and the adsorbent may be prepared as follows: the magnetic component such as 400 Series stainless steel particles and the adsorbent, e.g., the zeolite sieve, are admixed with a base for the adsorbent and a relatively homogeneous gel is formed. The adsorbent base may be comprised of, for example, silica, alumina or silica-alumina. The gel is then dried, calcined and sized. Suitable techniques for sizing and shaping the composite adsorbent are extrusion, pilling, beading, spray drying, etc. The magnetizable component may also be composited with the adsorbent by impregnation, cogelling, coprecipitation, etc.

The bed particles (composites or admixtures) will typically have an average mean particle diameter ranging from about 50 to about 1500 microns, preferably from about 100 to about 1000 microns, and more preferably from about 175 to about 850 microns. The particles may be of any shape, e.g., spherical, irregular shaped or elongated.

The application of a magnetic field to the fluidized particles containing the magnetizable particles in the adsorption or desorption zones in accordance with the invention is not limited to any specific method of producing the magnetic field. Conventional permanent magnets and/or electromagnets can be employed to provide the magnetic field used the practice of the present invention. The positioning of the magnets will, of course, vary with the solids used, degree of fluidization required and the effects desired. In the preferred embodiment of the present invention, a toroidally shaped electromagnet is employed to surround at least a portion of the fluidized bed as this provides the most uniform magnetic field and consequently the best stability throughout the bed. The electromagnets may be energized by alternating or direct current, although direct current energized magnetic fields are preferred. Such electromagnets when powered by direct current with the use of solid state control or transformer/rectifier are particularly desirable for applying a magnetic field to the bed particles and to provide an excellent method of stabilizing the fluidization of the bed particles in response to the flow of the fluidizing medium.

The process operating conditions to be employed in the practice of the present invention may vary and will include those reaction conditions typically employed in adsorption-desorption hydrocarbon separation processes. As well known, these conditions will generally vary depending on the hydrocarbon feed stream being treated, the adsorbent being used, etc. Generally speaking, the higher boiling hydrocarbon feeds will use higher temperatures and pressures. In its broadest sense, temperatures ranging from ambient to about 600° C., preferably from about 100° C. to about 500° C. and more preferably from about 250° C. to about 375° C., and pressures ranging from about 1 to about 1600 psig, preferably from about 150 to about 500 psig. The feed may be either in a gaseous or liquid state, but the gaseous state is preferred. The superficial fluid velocity of the fluidizing fluid (e.g., hydrocarbon feed) may range from about 0.01 to about 3 m/sec, more preferably from about 0.08 m/sec to about 1.5 m/sec. The bed particles preferably move countercurrently in a plug flow manner against the ascending feed or stripping gas by the action of gravity or pressure in the contactor. The solids circulation rate may vary depending on the level of straight chain hydrocarbons in the feed, the size of the vessels, the feed gas velocity, etc. However, it may range from about 1 K lb to about 5,000 K lb per hour or more.

The hydrocarbon feed mixture applicable to the process of the present invention is comprised of a mixture of two or more hydrocarbon components having from 3–30 carbon atoms per molecule. Examples of these hydrocarbon components are propane, butane, pentane, hexane, heptane, octane, nonane, decane, dimethylbutane, dimethyl-pentane, trimethyl-pentane, and other normal aliphatic hydrocarbons and their isomers; cyclohexane, decaline, tetraline and other alicyclic-hydrocarbons; benzene, toluene, xylene, diethylbenzene, ethyltoluene, trimethyl-benzene, butyl-benzene and other aromatic hydrocarbons such as alkyl benzene, or alkyl-naphthalene; industrial product of hydrocarbon mixtures of paraffin, naphtha or reformate which may also be referred to as ultraformer, platformer, Houdriformer or Rheniformer; pyrogasoline and other hydrocarbon derivatives from naphtha cracking process and those products yielded from distillation, alkylation or hydration processes. Both hydrocarbon mixtures comprising two or more compounds of different molecular weights, as well as the same molecular weights, that is, isomers, are included as a feed mixture. Examples of isomer mixtures are $C_5$ aliphatic isomers of dimethylpropane and pentane; $C_6$ aliphatic isomers of dimethylbutane, ethylbutane, methylpentane and hexane; $C_7$ aliphatic isomers of dimethylpentane, methylhexane and heptane; $C_8$ aliphatic isomers of trimethylhexane and octane, $C_8$ alicyclic isomers of dimethylcyclohexane and ethylcyclohexane. The process of the present invention is particularly suited for separating straight chain paraffins from recycle streams in $C_5/C_6$ recycle isomerization units. Another feed suited for the process of the present invention is a $C_9$–$C_{18}$ hydrocarbon fraction and more preferably $C_{10}$–$C_{15}$ kerosene fraction. Feed streams will contain normal paraffins, isoparaffins and aromatics in varying concentrations, depending on the type of crude from which the hydrocarbon fraction is derived and the carbon number range of the fraction. The normal paraffin concentration will typically range from about 20 to about 60 vol.% of the feed and the aromatic concentration will typically range from about 10 to about 30 vol.% of the feed, although the feed content may vary from these values. Since the feed aromatics, like the isoparaffins, cannot enter the pores of the adsorbent used in the process of the present invention because their cross-sectional diameter is too great, almost all of the aromatics appear in the raffinate stream. A small portion, however, is rather tenaciously adsorbed on the surfaces of the adsorbent particles and ultimately appears as a contaminant in the extract (normal paraffin) product.

The adsorption can take place in any suitable vessel as earlier mentioned. The vessel may be equipped with internal supports, trays, etc. In the lower portion of the adsorption vessel there will be disposed a suitable grid means for distributing the incoming hydrocarbon feed. The bottom or lower portion of the adsorption vessel will have means for removing spent solids from the adsorption vessel. This opening may be at the side of the vessel or at its bottom. Preferably a pipe grid is utilized for feeding the hydrocarbon feed, i.e., perforated pipes. By use of a pipe grid the spent solids may flow past the grid by gravity to the regenerator or desorber.

The adsorbed hydrocarbons can be desorbed by any one of the three known methods, i.e., thermal swing, pressure swing or purge cycle. The thermal swing process involves heating the spent particles to a temperature where the sieves adsorptive capacity for the straight chain hydrocarbons is reduced to a low level. The straight chain hydrocarbons are then easily removed by a purge gas stream. The pressure swing process involves reducing the beds total pressure and thereby the component partial pressure during desorption to reduce the sieves adsorption capacity while the bed temperature is held constant. The purge cycle process involves using another fluid during desorption to either strip or displace the adsorbed hydrocarbon from the sieve particles. Various known purging agents may be used in the process of the present invention, e.g. hydrogen gas, ammonia, steam, hydrocarbon gases, etc. Hydrogen is a preferred purge gas in the practice of the present invention. When hydrogen is used it is swept through the bed of spent particles. The hydrogen reduces the partial pressure of the adsorbed straight chain hydrocarbons. This results in a decrease in the adsorptive capacity of the sieve and the bed particles are thus stripped of the straight chain hydrocarbons. The desorbed straight chain hydrocarbons may be condensed from the hydrogen and the hydrogen is recompressed and recycled for further use as a purge gas. The condensed straight chain hydrocarbons are stabilized to remove both light gases and soluble hydrogen and are then recycled to an isomerization unit for further conversion or placed in a product stream. Depending on the type of product and product yields desired in a plant the process of the invention may be incorporated either upstream or downstream from the isomerization unit. This selection will generally depend on the feed available.

A specific generalized example of the process of the present invention comprises contacting a bed of particles of molecular sieves containing a ferromagnetic component countercurrently with a feed of vapors containing straight chain and non-straight chain hydrocarbons in the magnetically stabilized adsorption zone. The solids leave the adsorption zone with the straight chain hydrocarbons loaded virtually at equilibrium with the feed vapors. The nature of the molecular sieve structure prevents any significant adsorption of compounds other than the straight chain hydrocarbons. By use of the magnetically stabilized bed, it is possible to use smaller particles than in fixed bed processes and by use of these small particles, reduced diffusion resistance can be realized. Also, the size of the adsorption bed is relatively small compared to a fixed bed of conventional-sized sieve particles. The sieve particles flow from the adsorption zone to the magnetically stabilized bed main desorption zone where they move downward countercurrent to the main purge gas stream. By reduction of partial pressure of the straight chain hydrocarbon in the gas, the straight chain hydrocarbons are desorbed. As in the adsorption step, the small particle size reduces diffusion resistance and results in a very close approach to equilibrium between vapors and solids at any given point. Temperatures and pressures are nearly the same in all the zones. The gases leaving the adsorption and main desorption zones are sent individually to heat exchangers (supplying heat to the feed and purge gas) and final coolers where the branch chain and straight chain products are condensed and the purge gas stream is separated for recycle.

EXAMPLE 1

The following example illustrates the operation of the magnetically stabilized fluidized bed with continuous solids addition and removal. The tests illustrate the point, or locus of transition points, between the bubbling fluidized and stabilized fluidized regions in beds which have continuous solids addition and removal.

Figure 4:
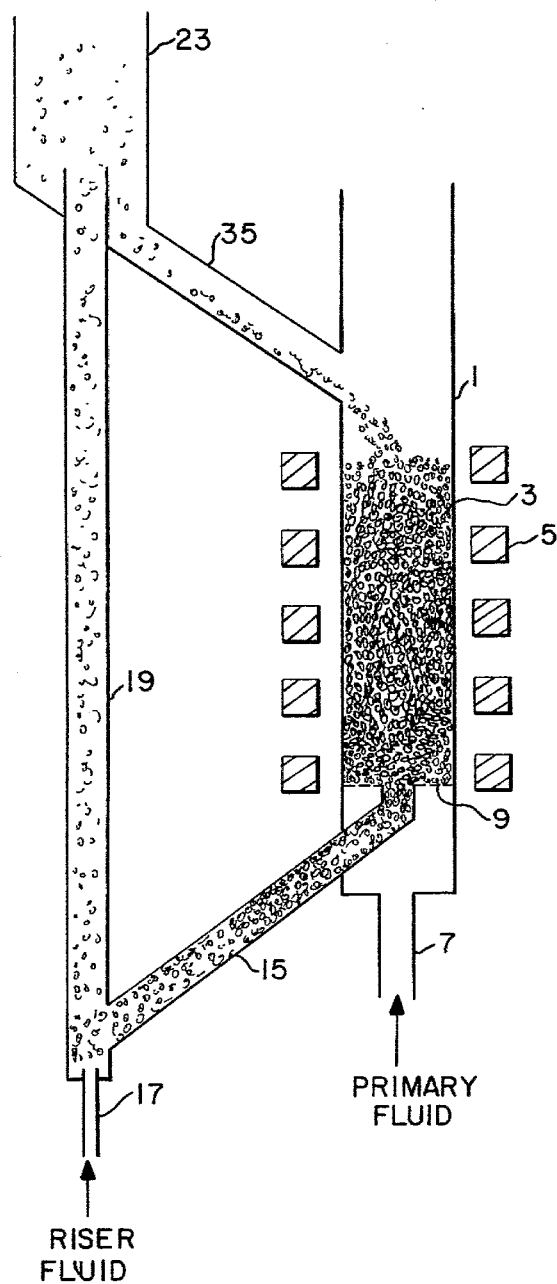
FIG. 4 represents a vertical cross-sectional view of an experimental device for continuously adding and removing magnetizable solids from the magnetic contacting vessel.

The equipment used in this study is schematically illustrated in FIG. 4. Contactor 1 is a Plexiglas vessel having a three inch inside diameter into which gas (air) is injected from below through pipe 7 and grid 9 into the bottom of the bed of magnetizable solids 3 to levitate the solids. In the continuous solids flow made, solids flow out of the bottom of the bed through the discharge system and the lower transfer tube 15 and then to riser 19. Larger gas (air) quantities from pipe 17 transport the solids up the one inch inside diameter plexiglass riser tube 19 and then into a three inch insider diameter solids disengaging section 23. The solids separate from the gas in the disengaging section 23 and then return to contactor 1 via solids transfer tube 35.

In the course of the studies conducted, two different solids discharge systems were used. The first type of discharge system used was a center discharge system. In this system, the solids exited from a one inch diameter hole in the center of the distributor. The second type of discharge system was a side discharge unit in which four one inch holes were located symmetrically around the bed 1.8 inches above the distributor through which solids could flow from the bed (only one of the ports of the four sided discharge system was used in these tests).

Once the solids would fall from the bed, they would enter the lower solids transfer tube 15. An orifice in this tube (not shown) was used to limit solids flow and prevent gas bypassing between the bed and riser.

Two six inch bore magnets collectively designated as 5 in FIG. 4 approximately four inches high were located around contactor 1. These magnets were placed approximately 10 cm apart. Each magnet consisted of 1110 turns of coated number twelve copper wire and had a resistance of about 3.78 ohms. These magnets were connected to a power supply (not shown) capable of providing a current in excess of six amperes.

The flow control system consisted of three DWYER rotameters for the fluidizing fluid (air) and three for the riser fluid. A pressure and temperature gage (not shown) were located just downstream of the rotameters to allow correction for gas density changes. The calibration of these rotameters was checked using wet and dry test meters.

A solids flow diversion valve (not shown) was located in the upper tube 35 returning solids to the bed. This valve was used to remove solids from the system and was also essential in determining an accurate solids circulation rate. The valve was constructed of brass and consisted of a simple flapper that would stop the return flow to the bed while discharging the solids through an opening in the bottom of the valve.

The material used in the tests was magnetite, purchased from Foote Mineral Company. When received the magnetite was sieved to a size between 60 and 80 U.S. sieve, corresponding to 177 to 250 microns. This material had an absolute density of about 5 grams/cc and a settled bed density of about 2.25 grams/cc, corresponding to a settled bed void volume of 0.55.

After the magnetite was sieved, it was placed into the continuous flow unit 1 and air was introduced via 7 and through the distributor 9 to leviate the bed. The minimum bubbling velocity was found by visual observation to be 8.5 cm/sec. Once the bed 3 was levitated, the air to the solids circulation system was turned on and solids could be continuously removed from the bottom of the unit, and reintroduced at the top. For batch bed runs, the circulation system was not used continuously, but provided a convenient means of removing solids through the solids sampling valve described above.

For the batch, non-circulating, bed runs the gas flow was first increased to the desired operating conditions, and then the magnetic-field was applied until the bed was stabilized. The height of the bed was then noted and the circulation system could be used to adjust it, by removing or adding solids, so that the test height of the bed at transition would be approximately 30.5 cm. Once the quantity of the material in the bed was so adjusted, the bed was refluidized without a magnetic field for a period of time exceeding 2 minutes.

The transition tests were run by setting the velocity of gas through the bed and then increasing the magnetic field intensity until the bed was stabilized. Bed stabilization, detected visually by cessation of bubbling in the bed, was quite reproducible for a single set of conditions. The gas velocity and magnetic field were then recorded giving one point on the transition locus from bubbling to stabilized beds. The magnetic field was then shut off and the bed refluidized for a period of time exceeding 2 minutes before the gas velocity was reset for a subsequent run. Batch bed results for the two discharge systems were obtained by the above described procedure as reference points for the circulating bed runs.

Transition conditions for continuous circulating beds were obtained similarly to the batch bed data, but of course with continuous solids addition and removal. The bed was first set for gas velocity and sufficient other gas was introduced to the solids circulation system to have a smooth flow of solids return to the bed. The magnetic field was then applied to stabilize the bed and the height noted. Solids would be added or removed from the system to adjust the height at the transition point to approximately 30.5 cm. The bed would then be fluidized without a magnetic field for a period in excess of 2 minutes.

For these tests, the solids circulation rate was measured. This was done using the solids sampling valve by removing a volume of solids for a measured interval of time. The solids were then weighed and the mass circulation rate calculated.

The rate of solids circulation could be adjusted by changing the size of the orifice located in the lower solids transfer line 15. Orifice hole sizes varied from ¾ inch to ¼ inch. Orifice thicknesses varied from ⅛ inch to ¼ inch for each hole size. The smaller and thicker orifice showed more resistance and this decreased the flow substantially.

Figure 5:
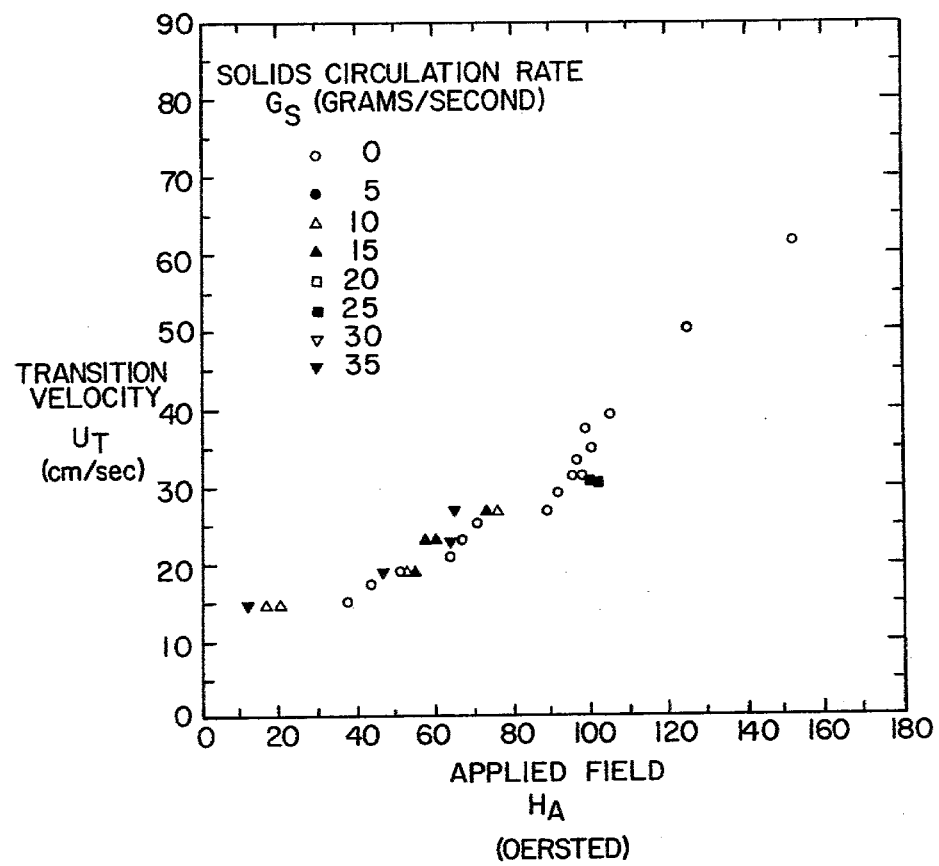
FIG. 5 represents transition superficial velocity as a function of applied magnetic field for batch and circulating beds using the apparatus of FIG. 4 with a center discharge unit.
Figure 6:
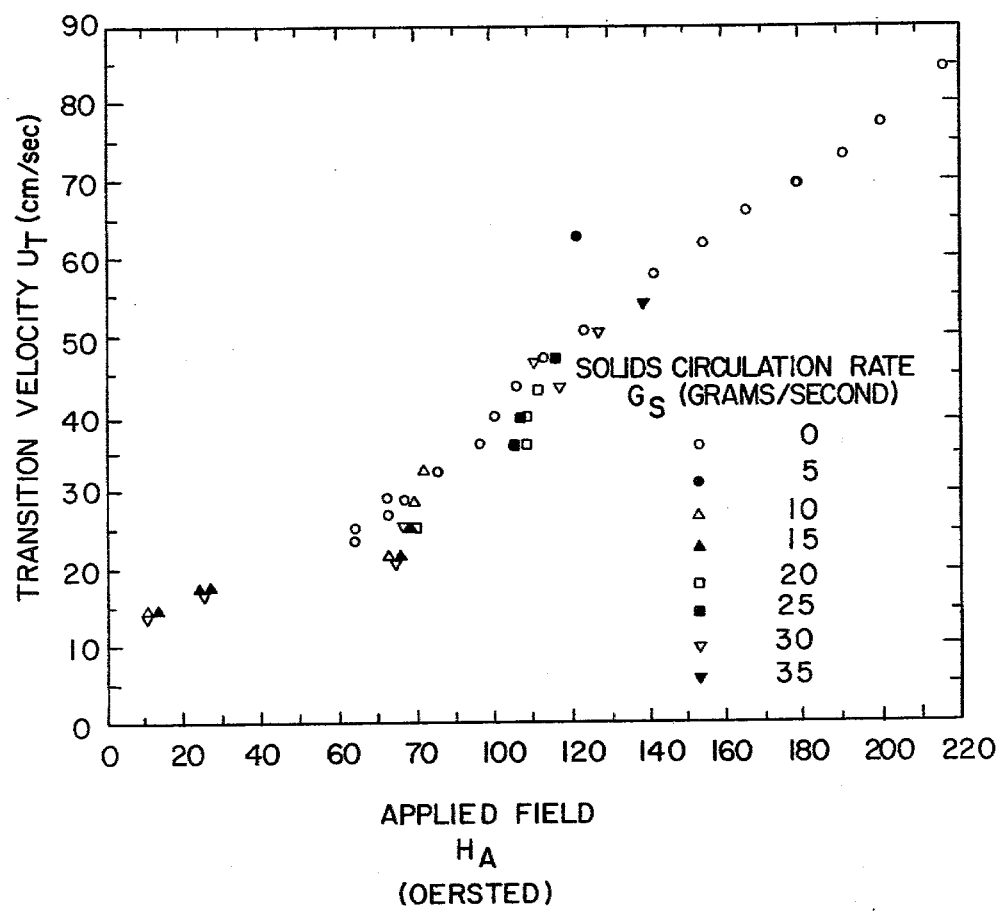
FIG. 6 represents transition superficial velocity as a function of applied magnetic field using the apparatus shown in FIG. 4 having a side discharge.

The results of the tests described above are presented in FIGS. 5 and 6. FIG. 5 illustrates transition velocity as a function of applied magnetic field for batch and circulating beds using the center discharge unit. Circulation rates as high as fifty grams a second were tested, corresponding to a bed turnover rate of about once every minute. It can be seen that solids circulation has no apparent effect on bed transition conditions for this discharge scheme. Similar results are presented in FIG. 6 for the side discharge unit. In both cases, circulating bed data could not be taken above about 100 to 120 oersted because of a decrease in bed fluidity causing solids plugging in the exit region of the bed.

During the transition tests with solids circulation, the solids entering the top of the bed were found to flow evenly across its surface with little difference in bed height from the point of solids addition. Visual observation of the sides of the bed detected no regions where solids flow was not taking place.

The results indicate no apparent effects of solids circulation rate on transition speed for the center and side discharge units. In otherwords, the same high velocities as in the batch beds can be reached at the same applied magnetic field for circulating beds. Also, similar to what has been found for batch bed systems using magnetite solids, the solids stopped (last fluidity) above an applied magnetic field of about 100 oersteds.

In other tests, it was discovered that the flowability of the magnetizable particles, at a given magnet field strength varies, depending on the magnetization of the particles used. For example, if a particle having a relatively low magnetization is used, e.g. G87RS nickel alloy, the particles are relatively fluid at high applied magnetic field strengths. However, particles such as iron and steel, unless composited with non-magnetic material have a tendency to agglomerate and cause bed stiffening at fields above 100 oersteds.

It was also found that by using an annular discharge system, the transition velocities were higher for beds with solids circulation than for batch beds. This effect, of course, is beneficial in applications. Thus, it might be inferred that bed movement, caused by the solids circulation, helps to more evenly distribute the fluid flow. In many applications, such as separations, there will be solids addition and removal, and thus some bulk movement of the bed particles, it is likely that non-uniformity in fluid distributors will cause no greater problems than in normal bubbling fluidized beds.

EXAMPLE 2

Flowability of Magnetized Solids

The ability to remove magnetized solids from a highly magnetized bed under certain conditions is of great importance in many applications using magnetically stabilized fluidized beds. With some types of magnetizable solids, such as iron and steel, the particle-to-particle attraction leads to stickiness in the bed that limits the solids fluidity in continuous units at values of magnetization M of the particle solids at values greater than about 500 gauss. In otherwords, with some magnetizable solids their fluidity decreases with increasing applied magnetic fields up to the point where the bed of magnetizable particles solidify as a slug. Low fluidity can cause flow stoppage and bed "locking" with adverse effects to the smooth operation of magnetically stabilized beds. Hence, bed fluidity is an important parameter for the rational design of a magnetically stabilized bed reactor system.

The following study characterizes bed fluidity as a function of applied magnetic field and operating conditions. It thus establishes the basis for operating the bed at or near the transition point between a stable bed and a bubbling bed mode.

The experiments conducted show that the angle of repose of the bed particles relative to that of a loosely packed bed can be used as a measure of fluidity. The angle of repose, $\beta$, is the angle the surface of a pile of solids makes with the horizontal. Depending on the method of determination, various angles of repose can be defined. The poured angle of repose is the maximum angle of the slope of a pile of solids poured from a funnel. Tilting angle of repose is the maximum angle of tilt of a bed of solids before sloughing occurs.

A characteristic feature of fluidized beds of cohesionless solids (solids without interparticle forces) is that their angle of repose, $\beta$, decreases gradually with increasing superficial velocity, U, from its initial value, $\beta_o$ at U=0, to zero at the minimum fluidization velocity $U_{mf}$. Thus, $$\tan \beta = \left(1 - \frac{U}{U_{mf}}\right) \tan \beta_o \quad (1)$$

The initial angle of repose, $\beta_o$, is approximately equal to the angle of internal friction, $\phi$, of a loosely packed bed. Thus, Equation (1) becomes $$\tan \beta = \left(1 - \frac{U}{U_{mf}}\right) \tan \tau \quad (2)$$

The tangent of $\phi$ is referred to as the coefficient of interparticle friction.

The decrease in the angle of repose with increasing velocity is due to the corresponding decrease in interparticle friction. When interparticle friction becomes very small or vanishes, the solids exhibit liquid-like behavior with very small or no resistance to shear and their angle of repose becomes zero.

The decrease of interparticle friction with increasing velocity is also reflected in the viscosity of incipiently fluidized beds. In these beds, the flow limit, i.e., the shear stress, to, below which the bed behaves as a rigid structure, decreases with increasing superficial velocity and approaches zero at minimum fluidization velocity. Below minimum fluidization, the bed is in a semifluidized state and resembles a Bingham plastic with an angle of repose and a flow limit greater than zero.

When interparticle cohesive forces are present, as in the case in magnetically stabilized beds, Equations (1) and (2) are not applicable. These cohesive forces, imparted by the magnetic field, alter the rheological characteristics of the magnetized solid particles and therefore affect the angle of repose.

EXPERIMENTAL DETERMINATION OF ANGLE OF REPOSE OF SOLIDS IN A MAGNETICALLY STABILIZED BED

The poured angle of repose was determined as follows. A 7.62 cm diameter open ended container was partially filled with magnetizable solids. A magnetic field was placed around the bed so as to provide a substantially uniform magnetic field. The bed was fluidized by passing air through a grid at the lower portion of the container. Additional magnetizable solids were poured into the container from a funnel that was raised as the heap of solids grew to cover the 7.62 cm diameter surface. The results of several tests are shown in Tables III, IV and V (shows tilting bed angle repose data).

At zero applied field, the angle of repose decreased with increasing velocity and approached zero at the minimum fluidization velocity. This is in agreement with Equations (1) and (2). When the applied field was greater than zero, the angle of repose similarly decreased with increasing velocity but approached zero at velocities much greater than the minimum fluidization velocity. Data extrapolation indicates that the angle of repose becomes zero at approximately the transition velocity. This suggests that a magnetically stabilized bed is not fully fluid until velocities above the transition velocity are attained, despite the fact that the pressure drop is approximately equal to bed weight above minimum fluidization. Below transition, the bed is in a semifluid state.

TABLE III
POURED ANGLE OF REPOSE

Material: 33 Wt. % RO Stainless Steel Beads
Particle Size: 192 μm
Particle Density: 2 g/cm³
Bed Height: 3.3~5.1 cm  Bed Diameter: 7.62 cm

| Applied Field Oersteds | Magnetization Gauss | Velocity cm/sec | Angle of Repose $\beta$ Degrees | Tan $\beta$ | Remarks |
|---|---|---|---|---|---|
| 0 | 0 | 0 | 31 | 0.60 | $U_{mf}$ = 5 cm/sec |
| 0 | 0 | 5 | ~3 | 0.06 | |
| 130 | 57 | 0 | 34 | 0.66 | $U_T$ = 12.8 cm/sec |
| 130 | 57 | 0 | 37.5 | 0.76 | |
| 130 | 57 | 4.4 | 22 | 0.40 | |
| 130 | 57 | 7.8 | 7.5 | 0.13 | |
| 130 | 57 | 7.8 | 6 | 0.10 | |
| 200 | 82 | 0 | 45 | 1.00 | $U_I$ = 17.2 cm/sec |
| 200 | 82 | 0 | 43 | 0.93 | |
| 200 | 82 | 4.3 | 34 | 0.66 | |
| 200 | 82 | 4.3 | 31 | 0.60 | |
| 200 | 82 | 7.8 | 18.5 | 0.33 | |
| 200 | 82 | 7.8 | | | |
| 200 | 82 | 10 | 15 | 0.26 | |
| 300 | 124 | 0 | 49 | 1.13 | $U_T$ = 26.0 cm/sec |
| 300 | 124 | 7.8 | 36 | 0.73 | |
| 300 | 124 | 14.2 | 25 | 0.46 | |
| 300 | 124 | 19.3 | 15 | 0.26 | |

TABLE IV
POURED ANGLE OF REPOSE

Material: Magnetite (CRL sample)
Particle Size: 266 μm
Particle Density: 5 g/cm²
Bed Height: 2.5~5 cm  Bed Diameter: 7.62 cm

| Applied Field Oersteds | Magnetization Gauss | Velocity cm/sec | Angle of Repose $\beta$ Degrees | Tan$\beta$ | Remarks |
|---|---|---|---|---|---|
| 0 | 0 | 0 | 39 | 0.80 | $U_{mf}$ = 13.7 cm/sec |
| 0 | 0 | 7.5 | 21 | 0.38 | |
| 0 | 0 | 12.3 | 9 | 0.15 | |
| 0 | 0 | 12.3 | 11.5 | 0.20 | |
| 65 | 210 | 0 | 41 | 0.86 | $U_T$ = 43.2 cm/sec |
| 65 | 210 | 12.8 | 34 | 0.66 | |
| 65 | 210 | 22.6 | 25 | 0.46 | |
| 65 | 210 | 38.6 | 8 | 0.13 | |
| 65 | 210 | 38.6 | 5 | 0.08 | |
| 130 | 380 | 0 | 45 | 1.0 | $U_T$ = 65.8 cm/sec |
| 130 | 380 | 0 | 47 | 1.06 | |
| 130 | 380 | 8.6 | 45 | 1 | |
| 130 | 380 | 19.3 | 41 | 0.86 | |
| 130 | 380 | 25.7 | 34 | 0.66 | |
| 130 | 380 | 45 | 15 | 0.26 | |
| 200 | 560 | 0 | 55 | 1.40 | |
| 200 | 560 | 0 | 51 | 1.26 | |

TABLE V
TILTING BED ANGLE OF REPOSE

Material: 33 Wt. % RO Stainless Steel Beads
Particle Size, Nominal: 177–425
Particle Density: 1.7 g/cm³
Bed Height: 3.8 cm  Bed Diameter: 3.8 cm

| Applied Field Oersteds | Velocity cm/sec | Angle of Repose $\beta$ Degrees | Tan$\beta$ | Remarks |
|---|---|---|---|---|
| 0 | 0 | 34 | 0.67 | |
| 0 | 4 | 4.5 | 0.078 | |
| 0 | 4 | 5 | 0.087 | |

TABLE V-continued
TILTING BED ANGLE OF REPOSE

Material: 33 Wt. % RO Stainless Steel Beads
Particle Size, Nominal: 177–425
Particle Density: 1.7 g/cm³
Bed Height: 3.8 cm  Bed Diameter: 3.8 cm

| Applied Field Oersteds | Velocity cm/sec | Angle of Repose βDegrees | Tanβ | Remarks |
|---|---|---|---|---|
| 150 | 4 | 20 | 0.36 | |
| 150 | 5 | 19 | 0.34 | |
| 150 | 6 | 10 | 0.17 | |
| 150 | 8.5 | 4.5 | 0.078 | |
| 300 | 4 | 30 | 0.58 | |
| 300 | 6 | 28 | 0.53 | |
| 300 | 8.5 | 24 | 0.44 | |
| 300 | 10.8 | 19 | 0.34 | |
| 300 | 13.5 | 14 | 0.25 | |
| 300 | 19.0 | 5.5 | 0.096 | |
| 480 | 4.5 | 42.5 | 0.91 | |
| 480 | 8.5 | 43 | 0.93 | |
| 480 | 13.5 | 37 | 0.75 | |
| 480 | 19.0 | 21 | 0.38 | |
| 480 | 23.0 | ~ | | Channeling at the wall |

The angle of repose increased with increasing magnetic field. At high fields and low-to-moderate velocities, the bed attained values that are higher than the angle of repose of loosely packed solids. This would imply that at high particle magnetizations, the fluidity in a magnetically stabilized bed is lower than that of packed beds. In the case of magnetite, at high applied fields, the bed was highly structured and needle formation was observed at the surface of the pile. The length of the needles increased with magnetization and sometimes reached the tip of the funnel.

THE EFFECT OF INTERPARTICLE COHESIVE FORCES ON BED FLUIDITY

The presence of interparticle magnetic forces in a magnetically stabilized bed gave rise to a bed structure with mechanical strength even in an expanded state. The particles were not "free floating" as in a conventional fluidized bed because each collision led to coherence between the colliding particles. The bed resembled a Bingham plastic with a flow limit much greater than zero. Increasing the magnetic forces increased the resistance to deformation and flow. Furthermore, due to dipole-dipole orientation of bed particles along the direction of applied field flow properties will be anisotropic. An analysis of the data in the Tables above indicates that the effect of these forces on bed fluidity manifests itself in the angle of repose. From this analysis, the angle of repose of the magnetized solids in a fluidized bed can be used as a measure of the relative fluidity of the solids in the magnetically stabilized bed.

A flow resistance index, R, is defined as follows $$R = \frac{\tan\beta}{\tan\phi} \approx \frac{\tan\beta}{\tan\beta_o} \quad (3)$$

where $\beta$ is the poured angle of repose measured at a given velocity and particle magnetization, $\beta_o$ is the poured angle of repose of loosely packed solids at $U=0$ and $M_p=0$, and $\phi$ is the angle of internal friction, taken equal to $\beta_o$. When R=0 the bed is fully fluidized and its fluidity is similar to that of an incipiently fluidized bed without a magnetic field. When R=1, bed fluidity should be essentially the same as the fluidity of a packed bed of solids. For $0<R<1$, the bed is in a semifluidized state with a fluidity between that of a packed bed and a fluidized bed. For R>1, bed fluidity would be less than that of a packed bed.

The flow resistance index is related to the static equilibrium of solids and does not directly address questions of solids flowability or dynamic viscosity once the solids are in motion. However, it seems reasonable that the solids viscosity would increase with increasing flow resistance index.

Using the data in the above tables for a bed of 192 micron 38 wt. % stainless steel beads at $H_A=300$ oersteds ($M_p=125$ gauss), the flow resistance index had the following values as a function of superficial velocity.

| U(cm/sec) | R |
|---|---|
| 0 | 1.85 |
| $U_{mf} = 5$ | 1.78 |
| $0.5\ U_t = 13$ | 0.83 |
| $0.8\ U_t = 21$ | 0.37 |
| $U_t = 26$ | 0.00 | where $U_t$=transition velocity (bubbling)).

It can be seen from the above that at superficial velocities of 50% of $U_t$ and greater, R approaches zero and at $U_t$ the bed, for all practical purposes, could be considered fully fluid.

These experimental results and a theoretical analysis of the same indicate that, due to interparticle magnetic forces, the fluidity of magnetically stabilized bed decreases with increasing particle magnetization, and decreasing bed expansion and superficial velocity. The angle of repose and/or the flow resistance index are a good indication of fluidity in a magnetically stabilized bed relative to that of packed and fully fluidized beds of the same solids.

When the flow resistance index approaches zero, the bed behaves like a true fluidized bed and flows readily under the influence of hydrostatic head. At flow resistance indices greater than about one, the resistance to flow is greater than a packed bed. For superficial velocities (or bed expansions) and magnetizations of practical interest for magnetically stabilized beds, the flow resistance index will probably be between zero and one, and the bed will resemble a semifluidized bed, even though bed pressure drop is approximately equal to bed weight. The semifluidized state in conjunction with the anisotropy of the bed will affect such parameters as solids viscosity, solids drag, solids discharge rates, solids stresses, etc.

Referring again to the drawings, FIG. 1 is shown for explanation of the principles of separation in the present invention. FIG. 1 shows a basic embodiment of the present invention wherein the feed comprising a hydrocarbon mixture is supplied to the bottom of vessel 1 containing a selectively adsorbing material and magnetizable component 3. A solenoid or magnet means 5 is arranged to supply a substantially uniform magnetic field on the solid particles 3 charged in vessel 1. The hydrocarbon mixture is supplied to the adsorber vessel via line 7. The hydrocarbon mixture from line 7 is fed directly to grid 9 (preferably a pipe grid, not shown) at a superficial fluid velocity sufficient to fluidize the bed particles. The bed particles leave vessel 1 in a descending manner via mass flow hopper 13 and standpipe 15. The flow of solids in the standpipe can be controlled by valve means in the standpipe (not shown). These bed particles are then transferred to desorber 23 via line 19. A lift gas from line 17 assists the transfer of the solids in line 19, whereupon the particles empty into desorber vessel 23 via outlet 21. The particles in desorber 23, in a fluidized state, move in a descending manner against the upflowing purge gas stream provided via line 31. The purge gas is fed directly to grid 25, preferably a pipe grid. The spent bed particles 3a are stabilized by a solonoid or magnet means 5a. The desorbed or regenerated bed particles flow out of vessel 23 countercurrently in a plug flow manner into mass flow hopper 29 via grid 25. The regenerated bed particles are then transferred to the adsorber vessel 1 via standpipe 33 and transfer pipe 35. Transfer of the bed particles is facilitated by a lift gas via line 17a. The bed particles are returned to vessel 1 via outlet 37. The nature of the selective adsorbent utilized in the process will permit the branched chains hydrocarbon to leave vessel 1 via line 11 while the straight chain hydrocarbons are adsorbed by the bed particles. The adsorbed hydrocarbons on the other hand are desorbed in desorber 23 and are emitted from the desorber via line 27 along with the purge gas. Inlets 21 and 37 are preferably tangential inlets which provide for a more homogeneous distribution of the bed particles in vessels 1 and 23. By use of this type of inlet the solids swirl into the vessel in a circular manner.

Figure 2:
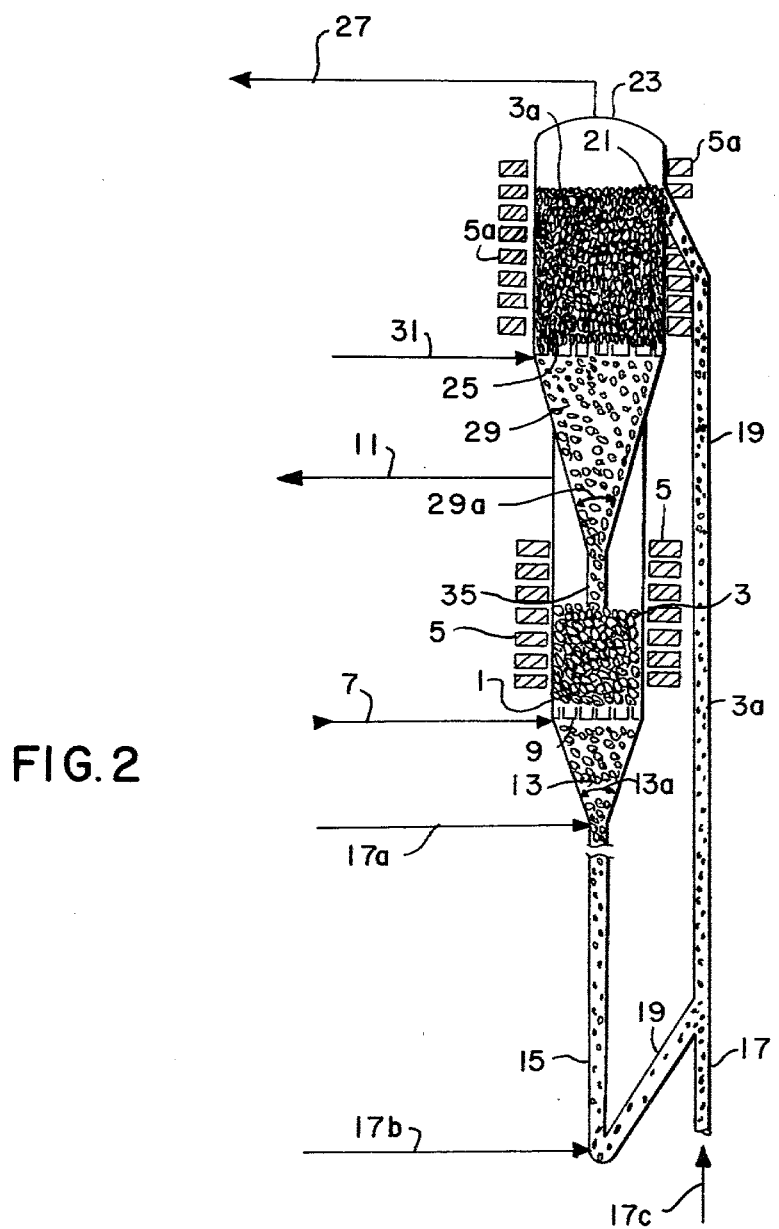
FIGS. 2 and 3 each represent a vertical front cross-sectional view of two magnetically stabilized contacting vessels wherein one contacting vessel is positioned above the other.

Referring to FIG. 2, there is shown a separation unit of the present invention which is suitable for the separation of n-paraffins from recycle stream in a $C_5/C_6$ recycle isomerization unit. A naphtha feed and magnetic 5A zeolite molecular sieve composite particles are fed into adsorption vessel 1 via lines 7 and 35, respectively. Adsorption vessel 1 is surrounded by electromagnetic torroidal coil 5 which is powered by a direct current source (not shown). Electromagnetic coil 5 is arranged to apply a substantially uniform field on the particle solids charged in adsorption vessel 1. The applied magnetic fields in this simulated process design are in Table VI. The bed particles are prepared by homogeneously mixing a slurry containing alumina gel, 400 Series stainless steel particles and 5A molecular sieve particles, drying and calcining the mixture followed by sizing to obtain spheres having an average particle diameter of about 200 microns. The fluidized magnetizable adsorbent particles exit vessel 1 in a descending manner via pipe grid 9 and enter mass flow hopper 13. Gas (e.g., hydrogen) is purged into standpipe 15 via lines 17a and 17b to provide optimum gasification and pressure buildup in the stand pipe. The spent particles are then transferred to desorber vessel 23 via line 19 aided by lift-/purge gas 17c from line 17. The spent particles 3a enter desorber 23 via a tangential inlet 21 and flow countercurrently in a plug flow manner against the ascending purge gas (e.g., hydrogen) fed to pipe grid 25 via line 31. The fluidized bed particles 3a in the desorber are stabilized by the action of the magnet coil 5a. The regenerated magnetizable adsorbent particles are recycled to adsorber 1 via mass flow hopper 29 and exit pipe 35. Mass flow hoppers 13 and 29 have an angle of 34° at 13a and 29a, an angle designed to provide the proper flow of solids based on the angle of repose of the particles. The branched chain hydrocarbons are emitted via line 11 and the straight chain hydrocarbons and purge gas are emitted via line 27. The operating conditions to be employed in the process scheme shown in FIG. 2 are shown in Table VI.

Figure 3:
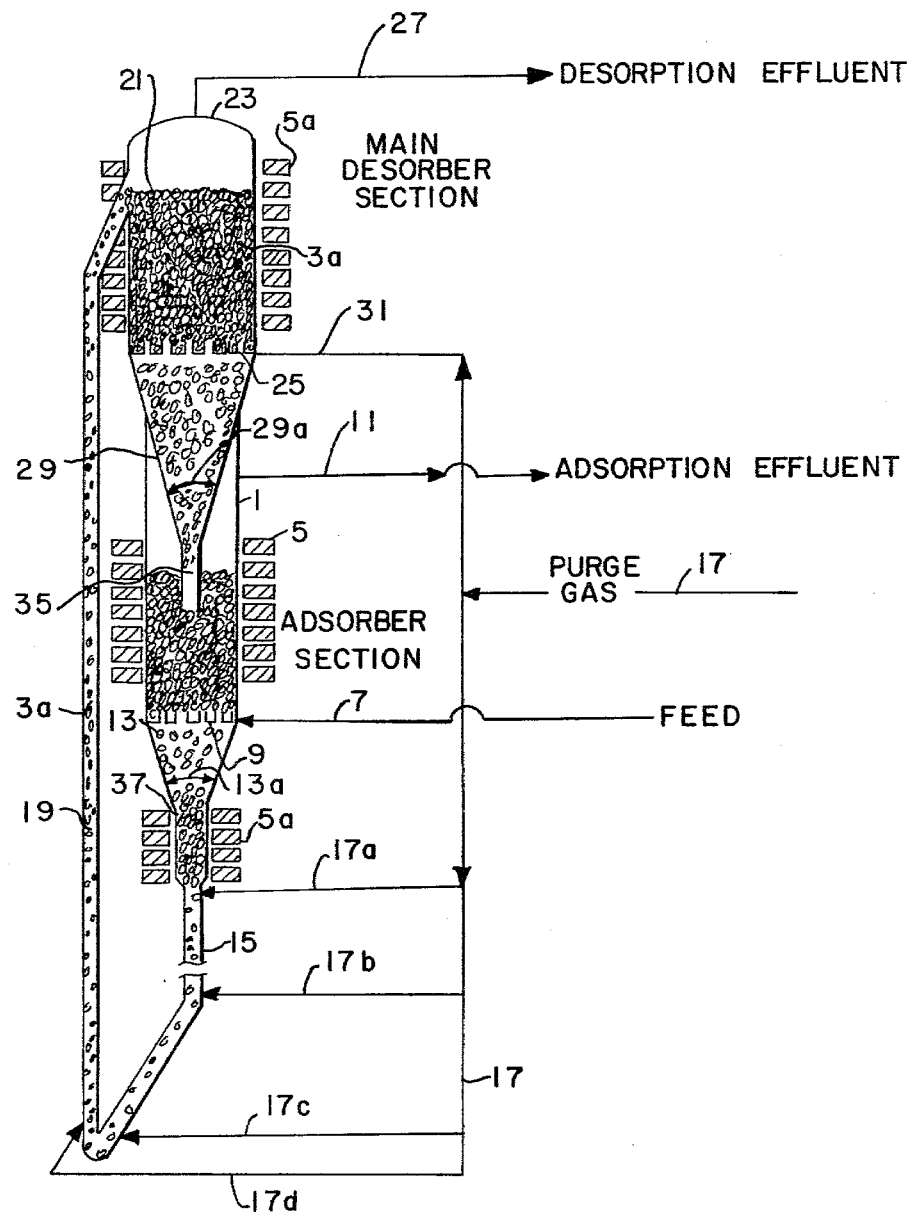

FIG. 3 shows substantially the same molecular sieve separation unit as shown in FIG. 2 except that FIG. 3 additionally includes a predesorber 37 magnetically stabilized by magnet means 5b and an additional lift-/purge gas line 17d. When predesorber is used it will be desirable to include a gas take-off pipe (not shown) at the top of the predesorber to remove the purge gas and desorbed straight chain hydrocarbons. The operating conditions to be employed in the process scheme shown in FIG. 3 are shown in Table VII.

As will be observed from the process operating conditions in Table VI the temperatures in the adsorber and desorber vessels may be different. This temperature differential can be attributed to the heat of adsorption in the adsorber which is removed during desorption. Thus, the overall process is generally isothermal. A more uniform temperature could be obtained by use of heat exchanger (not shown in the drawings). Also, if desired, a makeup sieve storage hopper may be situated between lines 15 and 19 in FIGS. 2 and 3 and connected by valve means to the lower portion of line 15.

The drawings do not show all lines, connections, instrumentation, valves, etc.

TABLE VI

PROCESS AND DESIGN CONDITIONS FOR STUDY DESIGN OF 28,300 B/SD MSB MOL SIEVE SEPARATION UNIT TO SEPARATE N-PARAFFINS FROM RECYCLE STREAM IN $C_5/C_6$ RECYCLE ISOMERIZATION UNIT [(1),(2),(3)]

(Line numbers refer to numerals in FIG. 2)

| Feed to Adsorption | Effluent From Adsorption | Desorption Gas to Lift Line | Desorption Gas to Vessel | Effluent From Desorption | Solids Circ. Rate |
|---|---|---|---|---|---|
| (Line 7) | (Line 11) | (Line 17c) | (Line 31) | (Line 27) | |
| 28.3 kB/SD | 192 k lb/hr. (n-paraffin content negligible) | 35 k lb/hr. | 86 k lb/hr. | 191 k lb/hr. | 1,207 k lb/hr. (excluding adsorbed hydrocarbons) |
| 262 k lb/hr (n-paraffin content 68 k lb/hr.) | 2.63 k mol/hr. | 2.92 k mol/hr. | 7.08 k mol/hr. | 10.9 k mol/hr. | |
| 3.55 k mol/hr. | 500° F. | 680° F. | 680° F. | 500° F. | |
| 500° F. | 300 psig | 310 psig | 310 psig | 300 psig | |
| 310 psig | 18.0 ACF/S | 30.8 ACF/S | 74.7 ACF/S | 97.0 ACF/S | |
| 26.7 ACF/S | | | | | |

FOOTNOTES:
[(1)] Solids Properties:    Av. particle size    200 microns
                         Particle density     1.53 g/cm$^3$
                         Wt. ratio sieve/ferromagnetic components: 75/25
                         Vol. ratio sieve/ferromagnetic components: 95/5

TABLE VI-continued
PROCESS AND DESIGN CONDITIONS FOR STUDY DESIGN OF 28,300 B/SD MSB MOL SIEVE SEPARATION UNIT TO SEPARATE N-PARAFFINS FROM RECYCLE STREAM IN $C_5/C_6$ RECYCLE ISOMERIZATION UNIT [1],[2],[3]

(Line numbers refer to numerals in FIG. 2)

| Feed to Adsorption | Effluent From Adsorption | Desorption Gas to Lift Line | Desorption Gas to Vessel | Effluent From Desorption | Solids Circ. Rate |
|---|---|---|---|---|---|
| | | Ferromagnetic component | 400 Series stainless steel | | |
| [2]Adsorber MSB Bed Conditions: | | Superficial gas velocity | 0.28 ft/sec. max | | |
| | | Bed height | 15.5 ft. | | |
| | | Bed diam. | 11.0 ft. | | |
| | | Void fraction | 0.50 | | |
| | | Applied magnetic field | 93 oersteds | | |
| [3]Desorber MSB Bed Conditions: | | Superficial gas velocity: | 0.40 ft/sec. max. | | |
| | | Bed height | 15.5 ft. | | |
| | | Bed diam. | 15.5 ft. | | |
| | | Void fract. | 0.50 | | |
| | | Applied magnetic field | 148 oevsteds | | |

TABLE VII
PROCESS AND DESIGN CONDITIONS FOR STUDY DESIGN of 35,300 B/SD MSB MOL SIEVE SEPARATION UNIT TO SEPARATE N-PARAFFINS FROM RECYCLE STREAM IN $C_5/C_6$ RECYCLE ISOMERIZATION Unit[1] [2] [3]

(Line numbers refer to numeral in FIG. 3)

| Feed to Adsorption | Effluent from Adsorption | Desorption Gas to Lift Line | Desorption Gas to Vessel | Effluent from Desorption | Desorption Gas Pre-Desorber Section |
|---|---|---|---|---|---|
| (Line 7) | (Line 11) | (Line 17c) | (Line 31) | (Line 27) | (Line 17a) |
| 35.3 kB/SD | 279.5 k lb/hr. | 2.6 k lb/hr. | 40.3 k lb/hr. | 100.4 k lb/hr. | 0.4 k lb/hr. |
| 336.6 k lb/hr. | (n-paraffin | 0.71 k mol/hr. | 11.05 k mol/hr. | 11.84 k mol/hr. | 0.10 k mol/hr. |
| (n-paraffin content 62 k | content negligible) | 700° F. | 700° F. | 700° F. | 700° F. |
| lb/hr.) | 4.33 k mol/hr. | 250 psig | 250 psig | 245 psig | 250 psig |
| 4.31 k mol/hr. | 700° F. | 9.3 ACF/S* | 144.3 ACF/S* | 158.8 ACF/S* | 1.3 ACF/S* |
| feed gas | 240 psig | | | | |
| 700° F. | 57.9 ACF/S* | | | | |
| 250 psig | | | | | |
| 56.2 ACF/S* | | | | | |

| | | |
|---|---|---|
| Solids Circ. Rate: | 2000 k lb/hr. (excluding adsorbed hydrocarbons) | |
| [1]Solids Properties: | Av. particle size | 200 microns |
| | Particle density | 1.53 g/cm$^3$ |
| | Wt. ratio sieve/ferromagnetic components: 75/25 | |
| | Vol ratio sieve/ferromagnetic components: 95/5 | |
| | Ferromagnetic component: | 400 Series stainless steel |
| [2]Adsorber MSB Bed Conditions: | Superficial gas velocity | 0.28 ft/sec. max. |
| | Bed height | 15.5 ft. |
| | Bed diam. | 11.0 ft. |
| | Void fraction | 0.50 |
| | Applied magnetic field | 93 oersteds |
| [3]Desorber MSB Bed Conditions: | Superficial gas velocity | 0.40 ft/sec. max. |
| | Bed height | 15.5 ft. |
| | Bed diam. | 15.5 ft. |
| | Void fraction | 0.50 |
| | Applied magnetic field | 148 oersteds |

*Actual cubic feet/sec. (vaporized feed gas)

As well known in the art of separations a number of variables should be considered in the course of designing a separation unit, e.g., adsorption equilibria, adsorption or desorption mass transfer rates, cyclic sieve life, unit scale up factors (i.e. unit size). In this regard, tests were carried out to study the equilibrium and kinetic characteristics of the vapor phase adsorption of n-hexane onto 5 A zeolite molecular sieve pellets. The gaseous system used in this evaluation was n-hexane/2,2-dimethyl butane/hydrogen because it is a relatively simple system which is representative of commonly used industrial systems. The experimental apparatus used was a fixed bed adsorber packed with 5 A zeolite molecular sieve as described in more detail below.

The sieve separation apparatus consisted of a 24 inch long, ¼" I.D. stainless steel tube that was packed with approximately 30 grams of 5 A molecular sieve particles. The packed column was placed in a hot box that was maintained at 400° F. (204° C.) by heated nitrogen. Hydrocarbon feed was fed in the tube at a precisely measured rate by a Ruska pump. The hydrocarbon feed was vaporized in the hot box by two 250 W cartridge heaters. The packed column was maintained at 220 psig by a GO, Inc. Model BP-3 pressure regulating valve which was specially designed to operate at 400° F. Ultra high purity hydrogen gas was fed into the column through a DP cell which measured the flow rate.

After the effluent exited the packed column and pressure regulating valve, it was mixed with a stream of $CO_2$ which was fed in at a precisely metered amount.

The effluent was then analyzed by a Baseline Industries Model 1030 BT online gas chromatograph with a Model SSP-1410 Control Module. The GC was calibrated to analyze for n-$C_6$, 2,2-DMB, and $CO_2$. By knowing the $CO_2$ flow rate, the flow rates of the n-$C_6$ and DMB could be calculated. After being analyzed by the GC, the effluent then went into a Dry Ice/acetone cooled cold finger condenser where most of the n-$C_6$ and DMB were condensed and collected in a tared flask. The remaining noncondensable gas coming out of the condenser was sampled for 5 seconds every minute by an automatic sampling valve and was put through a wet test meter. The gas samples were analyzed by mass spectroscopy to determine their composition. The resulting measurements enabled mass balances to be made for each component.

The sieve separation apparatus was operated in two modes—adsorption and desorption. Firstly, the sieve was saturated with the feed mixture, i.e., n-hexane/2,2-DMB/$H_2$ was fed in the tube until the GC analyses showed that the effluent composition had stopped changing. At that point the hydrocarbon flow was stopped and the $H_2$ rate was increased to begin stripping off the hydrocarbon adsorbed onto the sieve. This mode of operation was called the desorption step (simulated the desorption step). The desorption mode was generally run for twice the time that the adsorption mode took (i.e., up to about 30 minutes). Then the feed mixture of n-hexane/2,2-DMB/$H_2$ was again fed into the tube until the GC analyses showed that the effluent composition had stopped changing.

A number of adsorption-desorption cycles were made using 2 different 2,2-DMB/n-$C_6$ molar ratios, 60/40 and 80/20 feed flow rates ranging from 0.4 to 2.2 liquid cc/min., and three particle sizes of sieve, i.e., 200, 800 and 2400 microns. Data on the adsorption zone heights were taken and plotted as a function of superficial gas velocity based on inlet feed concentrations. The zone heights for all 3 particle sizes for the 80/20 2,2-DMB/m-$C_6$ ratio increased with increase in the superficial gas velocity. This was caused by the greater deviation from plug flow due to turbulent backmixing. The slopes of the 3 lines was all about 2, i.e., the zone heights vary directly with the square of velocity for these particle sizes and concentration. Schumacher et al., *I & EC Process Design & Development*, 6 (3), July, 1967, pp. 321-327, reported a slope of 0.64 for all particle sizes and hydrocarbon systems and Kehat et al., *I & EC Process Design & Development*, 4 (2), April, 1965 pp. 217-220, reported a slope of 0.57 for the benzene-n-$C_6$ system. An unexpected feature in the instant experiments was that the zone height line for the 800 micron size particle was below the 200 micron line. Theoretically, the smaller particle should have a smaller zone height due to easier intraparticle diffusion. One reason for this might be that the 200 micron and 800 micron sizes lie on the flat part of an effectiveness factor-particle size curve where intraparticle diffusion in not the rate-limiting step. The 2400 micron line was then considered to be on the part of the effectiveness factor-particle size curve where intraparticle diffusion is the rate-limiting step. The 2400 micron line differed from the 200 micron and 800 micron lines (taken as a group) by a factor of 2 to 4. Thus, potentially the contactor vessel volume in a moving magnetically stabilized bed could be halved by using a particle in the 200–800 micron size range instead of the 2400 micron size range.

All of the cycles made with a 60/40 s,s-DMB/n-$C_6$ molar ratio showed no variation of zone height with particle size. This unexpected result may be due to a breakdown of the theoretical treatment of the data since the hexane accounted for 40% mole of the hydrocarbon fed into the adsorber.

The mass transfer coefficients $K_y a$ were plotted as a function of inlet superficial velocity. In the expression $$N_{tog} = \int_{Y_B}^{Y_E} \frac{dY}{(Y - Y^*)}$$

wherein $N_{tog}$ is the number of overall gas phase transfer units in the adsorption zone and Y is the concentration of solute in the column effluent, g mole solute/g mole solvent, the simplifying assumption was made that n-$C_6$ adsorbed irreversibly, i.e., $Y^* = 0$. By making this assumption, the expression $$\int_{Y_B}^{Y_E} \frac{dY}{(Y - Y^*)} = \frac{Z_A}{(G_s/K_y a)} = N_{tog}$$

wherein Y is the concentration of solute in the column effluent, g mole solute/g mole solvent, can be directly integrated between $Y_B = 0.05$ and $Y_E = 0.95$ to yield $N_{tog} = 2.944$. In a plot of $K_y a$ vs. superficial velocity it was found that for a 80/20 2,2-DMB/n-$C_6$ molar ratio, the 800 micron particle size exhibits the highest values of $K_y a$. The 200 micron plot was slightly below it while the 2400 micron line was only one half as high. The reasons for this arrangement can be traced to the zone height calculations since $K_y a$ is inversely proportional to zone height. The same argument used to explain the clustering of the different particle size lines for a 60/40 2,2-DMB/n-$C_6$ ratio can also be used to explain the fact that for a 60/40 ratio, the $K_y a$'s do not vary with particle size. However, an unexpected result is that the $K_y a$'s for the 80/20 ratio appear to decrease with increasing velocity. Ordinarily, one would expect the $K_y a$'s to increase with velocity since any film resistance would tend to become smaller. However, this unexpected decrease of $K_y a$'s has also been reported by Kehat et al, supra. It is believed that increasing the flow rate would cause a decrease in the rate of adsorption. This decrease in rate would show up as a decrease in $K_y a$. In sum, the mass transfer coefficient for the 2400 micron sieve particles, independent of superficial velocity or feed composition at 400° F. and at 220 psig was:

$$K_a = 5.5 \text{ min}^{-1} \pm 1.5 \text{ (two sigma)}$$

whereas the mass transfer coefficients for 200 or 800 micron crushed sieve extrudates were too fast to measure, but at least 2.5 times faster than for the 2400 micron sieve extrudates. Thus, at 400° F. and at 220 psig, $$K_a > 14 \text{ min}^{-1}$$

The equilibrium cycles were made with fresh charges of molecular sieve, all of which had been flushed with pure $H_2$ for at least 12 hours except for one which had been flushed with $H_2$ for only 2½ hours at 400° F. and 150 psia. The difference between the total solvent in the feed and the cumulative solvent in the effluent was taken as the equilibrium loading on the molecular sieve particles.

These equilibrium loadings were plotted against n-$C_6$ partial pressure data. The n-$C_6$ partial pressure was calculated by multiplying the n-$C_6$ mole fraction in the feed by the reactor pressure. The curve was taken from equilibrium data provided by published literature for 5 A molecular sieve - n-$C_6$ adsorption at 400° F. It only goes up to 10 psia n-$C_6$ pressure. However, Rosenkranz and Kehat supra reported that the equilibrium curve approaches a value of 11 g. n-$C_6$/100 g. sieve. So by extrapolating this curve toward the 11 g./100 g. mark it was observed that three of the data points were rather close.

The following simulation exemplifies the preparation of a composition useful for the separation of paraxylene from an admixture of ethyl benzene, ortho-, meta-, and paraxylenes, and a process utilizing said composition to preferentially absorb the paraxylene from the admixture during passage of said admixture through a magnetically stabilized bed of potassium exchanged Type Y zeolite in the apparatus configuration shown in FIG. 1.

A commercial sodium-Y zeolite is exchanged hydrothermally three times, for 90 minute periods at 120° F., in an ammonium nitrate in water solution, the ammonium nitrate being present in the solution in three-fold excess based on the amount of sodium within the particles being exchanged. The Y zeolite, in each instance is washed free of excess ammonium nitrate with deionized water and then dried at 250° F. In this preparation 80 percent of the sodium is replaced by the ammonium ion.

The ammonium Y zeolite is placed within an open dish, and heated in air in a muffle furnace at 300° F. for one hour, and then in air and steam at 900° F. for an additional hour to decompose the ammonium cation.

The zeolite is then exchanged hydrotherminally three times with a solution containing potassium chloride, in three-fold excess based on the amount of potassium needed to exchange out the original sodium ions. Each exchange is conducted at 120° F. for 90 minutes, and the zeolite is recovered by filtration prior to the second and third exchanges. After the third exchange, the potassium exchanged zeolite is washed, dried, and calcined.

The potassium exchanged zeolite is then mulled with sufficient 410 stainless steel powder and alumina to form an extrudable mixture comprised of 30 wt. percent of the stainless steel powder, 60 wt. percent of the zeolite and 10 wt. percent alumina. This mixture is extruded through a 1/16 inch die, dried in an oven, and calcined in nitrogen at 750° F. for 3 hours. The calcined particles are then crushed and screened to obtain a 14–35 mesh (Tyler) fraction.

The magnesium adsorbent composition is then charged to the contacting vessels shown in FIG. 1 which is equipped with temperature control and heating systems (not shown). Adsorber 1 (which contains 5 theoretical plates) is charged with an equimolar mixture of m-xylene and p-xylene at a flow rate of 100 mols/-min. at 320° F. and at 1 atm. of pressure via pipe 7 and grid 9. The p-xylene is preferentially adsorbed by the ferromagnetic adsorbent particles which are stabilized by the magnetic field imposed by magnet means 5. A m-xylene enriched steam consisting of 98% m-xylene exits adsorber 1 via pipe 11 at a rate of 28.25 mols/min. and at a temperature of about 320° F. and at pressure of 1 atmosphere. The p-xylene saturated ferromagnetic adsorbent particles (which also contain a small amount of m-xylene) are continuously removed from adsorber 1 via standpipe 15. These particles are gasified and lifted by lift gas 17 to desorber 23 via pipe 19 and tangential outlet 21. The ferromagnetic adsorbent particles are regenerated in the desorber by steam stripping. Steam is injected into desorber 23 via pipe 31 at 320° F. The steam enters desorber 23 via pipe 31 and reduces the partial pressure of the adsorbed p-xylene and m-xylene. A p-xylene enriched stream and steam exit vessel 23 via pipe 27. The p-xylene enriched steam exits pipe 27 at a rate of 71.75 mols/minute and the stream contain 69.5% p-xylene. The ferromagnetic sorbent circulates through the system at a rate of 75 kg/minute, on a dry basis. If the sorbent circulation is reduced to 67.5 kg/minute, the m-xylene exits pipe 11 at a calculated rate of 35.94 mols/minute (94.4% m-xylene) and the p-xylene exits pipe 27 at a rate of 64.06 mols/min. (74.9% p-xylene). If the volume of the adsorber vessel 1 is doubled the calculated circulation rate is 66.5 kg/min. and m-xylene is recovered at a rate of 36.9 mol/min. (98% m-xylene) and the p-xylene is recovered at a rate of 63.07 mols/minute (78.1% p-xylene).

The above simulated examples illustrate the separation of linear hydrocarbons from branched hydrocarbons and the separation of m-xylene from p-xylene. It will be recognized that other separations may be practiced in accordance with the present invention, namely, separation of oxygen from air, separation of gas mixtures, e.g., ethylene from hydrocarbons, drying moist gases, separation of olefins, e.g., modification of the olefins in process to an MSB, separations of dienes, etc. In practicing any of these or other known separations, one simply employs the sorbent material, e.g., molecular sieve, etc., normally used for that purpose and prepares a composite of the sorbent and magnetizable particles. As such the sorption conditions such as temperature and pressure of commercially practiced fixed bed separation processes can be utilized. In the case of the instant process, the process is operated with a fluidized bed which permits the use of relatively small sorbent particles.

What is claimed is:

1. In a process for effecting fluid-solids contacting under fluidization conditions wherein a bed of suspended or levitated magnetizable particles are contacted within a contacting vessel with a fluid stream which passes through said bed in an ascending manner against the force of gravity, said bed being structured or stabilized by an applied magnetic field having a strength sufficient to suppress solids backmixing, the improvement which comprises: passing said bed of suspended magnetizable particles in a decending substantially countercurrent, plug-flow manner against said contacting stream, removing said bed particles from said contacting vessel, said process being operated in a manner such that the ratio of the difference between the transition velocity and the operating velocity to the difference between the transition velocity and the normal minimum fluidization velocity ranges between −0.1 to +0.5 so as to achieve enhanced solids fluidity.

2. The process of claim 1 wherein said magnetizable particles are continuously removed from said contacting vessel to a second contacting vessel and said contacting in the first and second contacting vessels being carried out in a substantially continuous countercurrent manner under plug-flow conditions in the presence of an applied magnetic field, and recirculating the magnetizable particles from said second contacting vessel to the first contacting vessel for further contacting.

3. The process of claim 2 wherein the fluid used in the first contacting vessel is different than the fluid in the second contacting vessel.

4. The process of claim 1 wherein said magnetizable bed particles are composites of nonferromagnetic material and ferromagnetic material.

5. The process of claim 1 wherein said magnetizable bed particles are admixed with nonferromagnetic material.

6. The process of claim 4 or 5 wherein the nonferromagnetic material has catalytic properties.

7. The process of claim 4 or 5 wherein the nonferromagnetic material has sorption properties.

8. The process of claims 1, 2, 3, 4 or 5 wherein a hydrocarbon is converted in said contacting vessel.

9. The process of claims 1, 2, 3, 4 or 5 wherein a sorption of at least one compound in said fluid is carried out in said contacting vessel.

10. The process of claims 3, 4 or 5 wherein said second contacting vessel is a regenerator wherein the catalytic or sorptive properties of the particles in the bed are regenerated and recirculated to the first contacting vessel.

11. The process of claim 1 wherein particulate solids entrained in the fluid stream are removed.

12. The process of claim 1 wherein a catalytic naptha reforming takes place in said contacting vessel.

13. The process of claim 1 wherein straight chain hydrocarbons are removed from branched chain hydrocarbons in said contacting vessel.

14. The process of claim 1 wherein p-xylene is separated from m-xylene in said contacting vessel.

15. The process of claims 4 or 5 wherein the nonferromagnetic material is a zeolite.

16. The process of claims 4 or 5 wherein the nonferromagnetic material is an activated carbon.

17. The process of claim 10 wherein a purge gas stream is employed in said regenerator.

18. The process of claim 10 wherein the purge gas is selected from the group consisting of hydrogen gas, ammonia, steam or hydrocarbon gases.

19. The process of claims 1, 2, 3, 4 or 5 wherein said fluid-stream is gaseous.

20. The process of claims 1, 2, 3, 4 or 5 wherein the process is operated in a manner such that the ratio of the difference between the transition velocity and the operating velocity to the difference between the transition velocity and the normal minmum fluidization velocity ranges between −0.05 and +0.2.

21. The process of claims 1, 2, 3, 4 or 5 wherein the process is operated in a manner such that the ratio of the difference between the transition velocity and the operating velocity to the difference between the transition velocity and the normal minimum fluidization velocity ranges between −0.01 and +0.1.

22. The process of claims 1, 2, 3, 4 or 5 wherein the bed is operated in the bubbling mode to effect improved heat transfer.

23. The process of claims 1, 2, 3, 4 or 5 wherein the bed particles have an average mean particle diameter ranging from about 50 to about 1500 microns.

24. The process of claims 1, 2, 3, 4 or 5 wherein the bed particles have an average mean particle diameter ranging from about 100 to about 1000 microns.

25. The process of claims 1, 2, 3, 4 or 5 wherein the bed particles have an average mean particle diameter ranging from about 175 to about 850 microns.

* * * * *

UNITED STATES PATENT OFFICE
CERTIFICATE OF CORRECTION

Patent No. 4,247,987    Dated  Feb. 3, 1981

Inventor(s)  Costas A. Coulaloglou and Jeffrey H. Siegell

It is certified that error appears in the above-identified patent and that said Letters Patent are hereby corrected as shown below:

In col. 3, line 41 and col. 4, line 29, change "$U_T-U_{op}/U_T-U_{mf}$" to $-- \dfrac{U_T-U_{op}}{U_T-U_{mf}} --$ In col. 6, line 34, change "$D_f$" to $-- d_f --$.

In col. 14, line 6, change "made" to -- mode --.

In col. 14, line 11, change "insider" to -- inside --.

In col. 16, line 9, change "last" to -- lost --.

In col. 17, line 17, change "$\tan \tau$" to -- $\tan \phi$ --.

In col. 18, line 21, change "$U_I$" to -- $U_T$ --.

Signed and Sealed this

Eleventh Day of October 1983

[SEAL]

Attest:

GERALD J. MOSSINGHOFF

Attesting Officer    Commissioner of Patents and Trademarks